US008633219B2

(12) United States Patent
Matsuzaki et al.

(10) Patent No.: US 8,633,219 B2
(45) Date of Patent: Jan. 21, 2014

(54) COMBINATION THERAPY

(75) Inventors: Yuji Matsuzaki, Osaka (JP); Wataru Watanabe, Osaka (JP); Satoru Ikeda, Osaka (JP); Mitsuki Kano, Osaka (JP)

(73) Assignee: Japan Tobacco Inc., Tokyo (JP)

( * ) Notice: Subject to any disclaimer, the term of this patent is extended or adjusted under 35 U.S.C. 154(b) by 2335 days.

(21) Appl. No.: 11/133,463

(22) Filed: May 20, 2005

(65) Prior Publication Data

US 2005/0288326 A1 Dec. 29, 2005

Related U.S. Application Data

(60) Provisional application No. 60/572,969, filed on May 21, 2004.

(51) Int. Cl.
*A61K 31/47* (2006.01)
*A61K 31/675* (2006.01)
*A61K 31/504* (2006.01)
*C07D 401/04* (2006.01)

(52) U.S. Cl.
USPC .............. 514/312; 514/81; 514/269; 514/256

(58) Field of Classification Search
USPC .................................. 514/312, 81, 256, 269
See application file for complete search history.

(56) References Cited

U.S. PATENT DOCUMENTS

| | | | |
|---|---|---|---|
| 3,472,859 | A | 10/1969 | Lesher et al. |
| 5,985,894 | A | 11/1999 | Clemence et al. |
| 6,248,736 | B1 | 6/2001 | Turner et al. |
| 6,248,739 | B1 | 6/2001 | Turner et al. |
| 7,176,220 | B2 * | 2/2007 | Satoh et al. .................. 514/312 |
| 2002/0103220 | A1 | 8/2002 | Schnute |
| 2004/0127708 | A1 | 7/2004 | Fuji et al. |
| 2005/0054645 | A1 | 3/2005 | Miyazaki et al. |
| 2005/0239819 | A1 | 10/2005 | Satoh et al. |

FOREIGN PATENT DOCUMENTS

| | | |
|---|---|---|
| EP | 498721 B1 | 8/1992 |
| EP | 1140851 | 10/2001 |
| EP | 1 564 210 A1 | 8/2005 |
| JP | A-48-26772 | 9/1973 |
| JP | 4-360872 A2 | 12/1992 |
| JP | A-2002-534416 | 10/2002 |
| JP | A-2002-534417 | 10/2002 |
| WO | WO 00/40561 | 7/2000 |
| WO | WO 00/40563 | 7/2000 |
| WO | WO 01/98275 A2 | 12/2001 |
| WO | WO 02/36734 | 5/2002 |
| WO | WO 02/055079 | 7/2002 |
| WO | WO 02/070486 | 9/2002 |

OTHER PUBLICATIONS

Eisenberg et al. "metabolism of GS-7340, a novel phenyl monophosphoramidate intraacellular prodrug of PMPA, in blood,"
Nucleosides, Nucleotides and Nucleic Acids, 2001, vol. 20, pp. 1091-1098.*
Clercq "Antiviral drugs: Current state of the art," Journal of Clincial Virology, 2001, vol. 22, pp. 73-89.*
Steinhart "Recent advances in the treatment of HIV/AIDS," Expert. Rev. Anti-infect. Ther. Feb. 2004, vol. 2, No. 2, pp. 197-211.*
Gilead Sciences Inc. "Gilead Sciences to Acquire Triangle Pharmaceuticals for $464 million Gilead to launch Coviracil in 2003 will Develop Co-Formulation of Viread and Coviracil,", 2002.*
Baker, Journal of Medicinal Chemistry, table 1, vol. 15, No. 3, pp. 235-237, 1972.
Chou and Talalay, Adv. Enzyme Regul. 22:27-55, 1984.
Guidelines for the Use of Antiretroviral Agents in HIV-Infected Adults and Adolescents, Aug. 13, 2001.
Hirao, I. et al., *Studies on the Synthesis of Quinoline Compounds, I.* Memoirs Kyushu Inst. Tech. (Eng.), 14:13-16, 1984.
Hirao, I. et al., *Antibacterial Activities of Oxodihydroquinoline Carboxylic Acid Derivatives*, Memoirs Department of Engineering, 14:21-32, 1990.
Mol. Pharmacol. 10:235-247, 1974.
Vincent, K.A., et al., *Characterization of Human Immunodeficiency Virus Type I Integrase Expressed in Eschericia coli and Analysis of Variants with Amino-Terminal Mutations*, J. Virol. 67: 425-437 (1993).
International Search Report for PCT/JP2005/009719 dated Sep. 14, 2005.
Boffito et al., "Lack of Pharmacokinetic Drug Interaction between Tenofovir Disoproxil Fumarate and Nelfinavir Mesylate" Antimicrob Agents Chemother., 49(10):4386-89 (2005).
Gerber, "Using Pharmacokinetics to Optimize Antiretroviral Drug-Drug Interactions in the Treatment of Human Immunodeficiency Virus Infection," Clin Infect Dis., 30(Suppl 2):S123-9 (2000).
Kearney et al., "Tenofovir disoproxil fumarate: clinical pharmacology and pharmacokinetics," Clin Pharmacokinet., 43(9):595-612, abstract only (Jun. 2004).
Kruse et al., "The steady-state pharmacokinetics of nelfinavir in combination with tenofovir in HIV-infected patients," Antivir Ther., 10(2):349-55 (2005).
McNicholl, "Drug Interactions Among the Antiretrovirals," Curr Infect Die Rep., 6(2):159-62 (Apr. 2004).

(Continued)

*Primary Examiner* — Shengjun Wang
(74) *Attorney, Agent, or Firm* — Finnegan, Henderson, Farabow, Garrett & Dunner, LLP

(57) ABSTRACT

The present invention relates to a combination therapy for treating an HIV infection or inhibiting integrase comprising (S)-6-(3-Chloro-2-fluorobenzyl)-1-(1-hydroxymethyl-2-methylpropyl)-7-methoxy-4-oxo-1,4-dihydroquinoline-3-carboxylic acid ("Compound A") or a pharmaceutically acceptable solvate or salt thereof in combination with at least one other anti-HIV agent. In some embodiments of the present invention, the other anti-HIV agents are chosen from reverse transcriptase inhibitors and protease inhibitors. In certain embodiments of the present invention, the other anti-HIV agents are chosen from AZT, 3TC, PMPA, efavirenz, indinavir, nelfinavir, a combination of AZT/3TC, and a combination of PMPA/3TC. Since Compound A has a high inhibitory activity specific for integrases, when used in combinations with other anti-HIV agents it can provide a combination therapy with fewer side effects for humans.

6 Claims, 8 Drawing Sheets

(56) References Cited

OTHER PUBLICATIONS

Piscitelli and Gallicano, "Interactions Among Drugs for HIV and Opportunistic Infections," N. Engl J Med., 344(13):984-96 (2001).

Seden et al., "Antiretroviral drug interactions: often unrecognized, frequently unavoidable, sometimes unmanageable," J Antimicrob Chemother., 64(1)5-8 (2009).

Song et al., "Lack of Interaction Between the HIV Integrase Inhibitor S/GSK1 349572 and Tenofovir in Healthy Subjects," Antimicrob Agents Chemother., 54(1):254-58 (2010).

Taburet et al., "Interactions between Atazanavir-Ritonavir and Tenofovir in Heavily Pretreated Human Immunodeficiency Virus-Infected Patients," Antimicrob Agents Chemother., 48(6):2091-96 (Jun. 2004).

Viread Package Insert (Nov. 2012).

Wenning et al., "Lack of a Significant Drug Interaction between Raltegravir and Tenofovir," Antimicrob Agents Chemother., 52(9):3253-58 (2008).

\* cited by examiner

COMBINATION THERAPY

CROSS-REFERENCE TO RELATED APPLICATIONS

This application claims the benefit of priority under 35 U.S.C. §119(e) to U.S. Provisional Application 60/572,969 filed May 21, 2004, which is incorporated herein by reference.

TECHNICAL FIELD

The present invention relates to a combination therapy for treating an HIV infection or inhibiting integrase comprising (S)-6-(3-Chloro-2-fluorobenzyl)-1-(1-hydroxymethyl-2-methylpropyl)-7-methoxy-4-oxo-1,4-dihydroquinoline-3-carboxylic acid ("Compound A") or a pharmaceutically acceptable solvate or salt thereof in combination with at least one other anti-HIV agent. In some embodiments, the present invention relates to the use of a combination comprising Compound A or a pharmaceutically acceptable solvate or salt thereof in combination with at least one other anti-HIV agent chosen from reverse transcriptase inhibitors and protease inhibitors. When used in combinations with other anti-HIV agents, Compound A can provide a combination therapy with fewer side effects for humans than existing therapies.

BACKGROUND ART

HIV (Human Immunodeficiency Virus), a retrovirus, is a causative virus of AIDS (Acquired Immunodeficiency Syndrome). HIV targets CD4 positive cell groups such as helper T cell, macrophage and dendritic cell and destroys these immunocompetent cells to cause immunodeficiency.

Accordingly, a pharmaceutical agent that eradicates HIV in the body or suppresses its growth is effective for the treatment or prevention of AIDS.

HIV possesses a bimolecular RNA gene in a core protein, which is covered with an envelope protein. The RNA codes for several enzymes (protease, reverse transcriptase, integrase) and the RNA has translated reverse transcriptase and integrase in the core, as well as protease inside and outside the core.

HIV attaches to and invades a host cell, becomes uncoated, and releases a complex of RNA and integrase into the cytoplasm. From the RNA, DNA is transcribed by reverse transcriptase, and a full length double stranded DNA is produced. The DNA is imported into the nucleus of the host cell and integrated by integrase into the DNA of the host cell. The integrated DNA is converted to an mRNA by polymerase of the host cell. Various proteins necessary for forming a virus are synthesized from the RNA by HIV protease, and a virus particle is finally formed, which then undergoes budding and is released from the host cell.

These virus specific enzymes are considered to be essential for the growth of HIV. These enzymes are drawing attention as the target of the development of antiviral agents, and several anti-HIV agents have been already developed.

For example, zidovudine (AZT), didanosine, lamivudine (3TC), and the like have been already on the market as reverse transcriptase inhibitors, and indinavir and nelfinavir as protease inhibitors.

In addition, a multiple drug combination therapy concurrently using these pharmaceutical agents has been employed. For example, a combined use of two reverse transcriptase inhibitors (zidovudine and didanosine) has been used clinically. A combined use of three agents of reverse transcriptase inhibitors (zidovudine and lamivudine) and a protease inhibitor (nelfinavir) and other pharmaceutical agents have also been clinically applied. Such multiple drug combination therapy is becoming a mainstream of AIDS therapy (see, e.g., Guidelines for the Use of Antiretroviral Agents in HIV-Infected Adults and Adlescent. Aug. 13, 2001).

However, some of these pharmaceutical agents are known to cause side effects such as liver function failure, central nervous disorders (e.g., vertigo), etc. In addition, acquisition of resistance to a pharmaceutical agent causes a problem. Even worse, emergence of an HIV that shows multiple drug resistance in a multiple drug combination therapy has been known.

Under the circumstances, a further development of a novel pharmaceutical agent, particularly a development of an anti-HIV agent based on a new mechanism, has been desired. Specifically, it has been a goal to develop an anti-HIV agent having an integrase inhibitory activity, because an integrase characteristic of retrovirus is an essential enzyme for the growth of HIV.

Nevertheless, there is a need to identify effective integrase inhibitors.

The present invention overcomes one or more of these needs and provides further related advantages.

Known compounds different from Compound A of the present invention are described in the following.

WO02/0704865 describes the following compounds (B1), (B2), and the like as anti-HIV agents having an integrase inhibitory activity (see WO02/0704865 p. 118, Example I-62, p. 203, Example I-152).

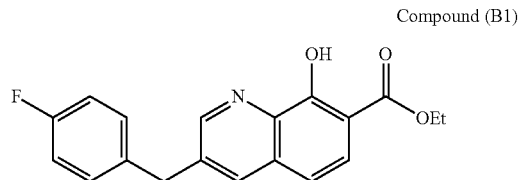

Compound (B1)

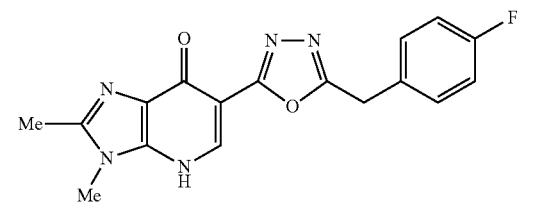

Compound (B2)

In addition, WO02/36734 describes the following compound (B3), and the like as anti-HIV agents having an integrase inhibitory activity (see WO02/36734, p. 106, Ex. 3).

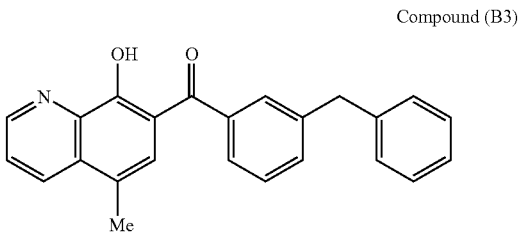 [SMILES: Cc1cc(C(=O)c2cccc(Cc3ccccc3)c2)c(O)c2ncccc12]

Compound (B3)

Moreover, WO02/55079 describes the following compound (B4), and the like as anti-HIV agents having an integrase inhibitory activity (see WO02/055079, p. 79, Ex. 1).

Compound (B4)

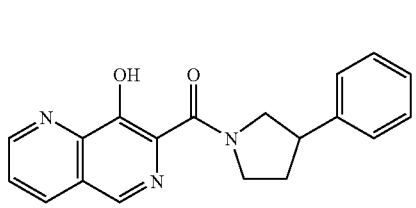

However, these publications do not include (S)-6-(3-Chloro-2-fluorobenzyl)-1-(1-hydroxymethyl-2-methylpropyl)-7-methoxy-4-oxo-1,4-dihydroquinoline-3-carboxylic acid ("Compound A") disclosed in the present specification, or any description suggestive thereof.

U.S. Pat. No. 3,472,859 describes the following compound (B5), and the like as antibacterial agents or antimicrobial agents (see U.S. Pat. No. 3,472,859, column 11, line 10).

Compound (B5)

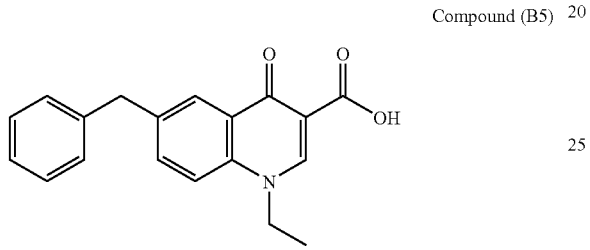

In addition, JP-A-48-26772 describes the following compound (B6), and the like as compounds having an antibacterial activity (see, e.g., JP-A-48-26772, p. 6, Example 9; KYUSHU KYORITSU UNIVERSITY, Memoirs Department of Engineering, No. 14, pp. 21-32, March 1990; Memoirs Kyushu Inst. Tech. (Eng.) No. 14, pp. 13-16, 1984).

Compound (B6)

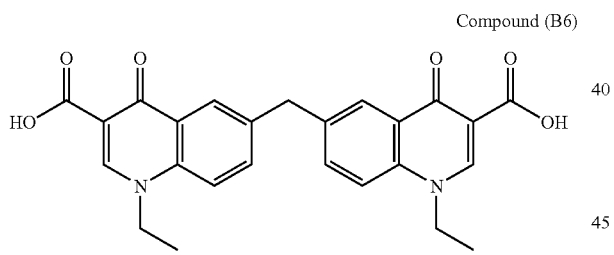

As dehydrogenase inhibitors, moreover, the following compound (B7), and the like have been pharmacologically evaluated (see Journal of Medicinal Chemistry, table 1, vol. 15, No. 3, pp. 235-237, 1972).

Compound (B7)

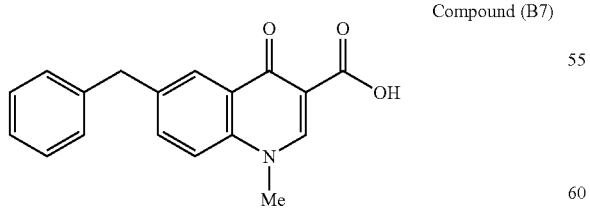

In addition, JP-A-2002-534416 (patent family: WO00/40561, U.S. Pat. No. 6,248,739, EP1140850) describes the following compound (B8), and the like as synthetic intermediates for compounds having an antiviral activity (see JP-A-2002-534416, p. 141, compound 60).

Compound (B8)

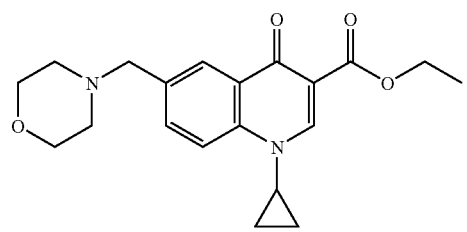

JP-A-2002-534417 (patent family: WO00/40563, U.S. Pat. No. 6,248,736, EP1140851) also describes the following compound (B9), and the like as synthetic intermediates for compounds having an antiviral activity (see JP-A-2002-534417, p. 34, compound 18).

Compound (B9)

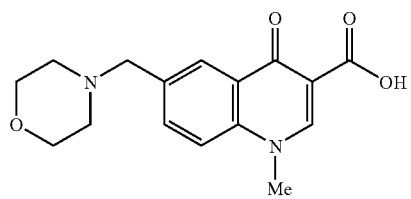

Moreover, WO01/98275 (patent family: U.S. 2001/103220) also describes the following compound (B10), and the like as synthetic intermediates for compounds having an antiviral activity (see WO01/98275, p. 39, line 29).

Compound (B10)

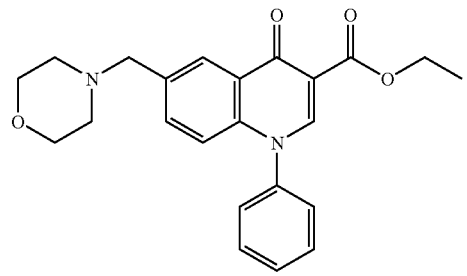

Furthermore, JP-A-4-360872 (patent family: U.S. Pat. No. 5,985,894, EP498721B1) describes the following compound (B11), and the like as compounds having an antagonistic action against anti-angiotensin II receptor (see JP-A-4-360872, p. 64, Table 1)).

Compound (B11)

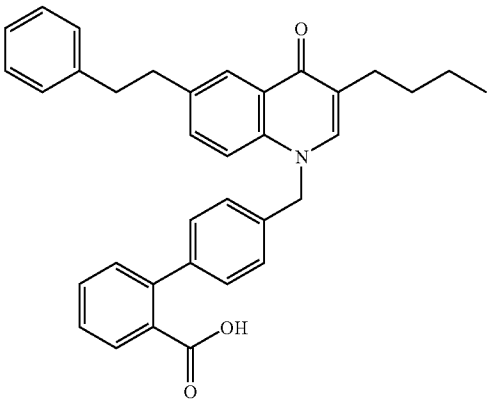

SUMMARY OF THE INVENTION

The inventors have discovered that the combination of (S)-6-(3-Chloro-2-fluorobenzyl)-1-(1-hydroxymethyl-2-methylpropyl)-7-methoxy-4-oxo-1,4-dihydroquinoline-3-carboxylic acid ("Compound A") or a pharmaceutically acceptable solvate or salt thereof with at least one other anti-HIV agent is highly effective as a combination therapy for treating an HIV infection or inhibiting integrase. The novel antiviral combinations of the present invention provide a way of treatment which may reduce the effective dose of either drug required for antiviral activity, thereby reducing cytotoxicity, but may also improve the absolute antiviral effect as a result of attacking the virus through multiple mechanisms. Similarly, the novel antiviral combinations provide a way for circumventing the development of viral resistance to a single therapy, thereby providing the clinician with a more efficacious treatment.

It is therefore an object of the present invention to provide a combination of pharmaceutical agents having an anti-HIV action. The mechanisms of action of the pharmaceutical agents having an anti-HIV action may be the same or different. In one embodiment of the present invention, the combination comprises one pharmaceutical agent having integrase inhibitory action and at least one other pharmaceutical agent having viral inhibitory action different from integrase inhibitory action. Some embodiments of the present invention include a combination of pharmaceutical agents having (a) integrase inhibitory action and (b) reverse transcriptase inhibitory action, protease inhibitory action, or both.

The present inventors have conducted intensive studies in an attempt to find a compound having an anti-HIV action, particularly a compound having an integrase inhibitory action having enhanced efficacy when used in combination with at least one other anti-HIV agent, and completed the present invention. Accordingly, examples of embodiments of the present invention include, and are not limited to, the following.

[1] A method for treating an HIV infectious disease comprising administering the combination of (a) and (b) to a mammal, wherein
(a) is an effective amount of (S)-6-(3-Chloro-2-fluorobenzyl)-1-(1-hydroxymethyl-2-methylpropyl)-7-methoxy-4-oxo-1,4-dihydroquinoline-3-carboxylic acid or a pharmaceutically acceptable solvate or salt thereof, and
(b) is an effective amount of at least one other anti-HIV active substance.

[2] The method of [1], wherein the at least one other anti-HIV active substance comprises at least one reverse transcriptase inhibitor.

[3] The method of [2], wherein the at least one reverse transcriptase inhibitor is chosen from zidovudine (AZT), lamivudine (3TC), tenofovir (PMPA), and efavirenz.

[4] The method of [2], wherein the at least one reverse transcriptase inhibitor is a combination chosen from (i) AZT combined with 3TC and (ii) PMPA combined with 3TC.

[5] The method of [1], wherein the at least one other anti-HIV active substance comprises at least one protease inhibitor.

[6] The method of [5], wherein the at least one protease inhibitor is chosen from indinavir and nelfinavir.

[7] The method of [1], wherein said administration of (a) and (b) is sequential.

[8] The method of [1], wherein said administration of (a) and (b) is simultaneous.

[9] The method of [1], wherein said administration of at least one of (a) and (b) is oral.

[10] The method of [1], wherein said administration of at least one of (a) and (b) is parenteral.

[11] The method of [10], wherein said parenteral administration is intravenous.

[12] The method of [1], wherein (a) and (b) are formulated together and administered as a single therapeutic composition.

[13] The method of [1], wherein the at least one other anti-HIV active substance is an inhibitor of HIV-1 protease.

[14] The method of [1], wherein (a), (b), or both (a) and (b) are administered daily.

[15] The method of [1], wherein said effective amount of (S)-6-(3-Chloro-2-fluorobenzyl)-1-(1-hydroxymethyl-2-methylpropyl)-7-methoxy-4-oxo-1,4-dihydroquinoline-3-carboxylic acid or a pharmaceutically acceptable solvate or salt thereof is in the range from about 0.01 mg to about 1 g per administration.

[16] A method for inhibiting integrase comprising administering the combination of (a) and (b) to a mammal, wherein
(a) is an effective amount of (S)-6-(3-Chloro-2-fluorobenzyl)-1-(1-hydroxymethyl-2-methylpropyl)-7-methoxy-4-oxo-1,4-dihydroquinoline-3-carboxylic acid or a pharmaceutically acceptable solvate or salt thereof, and
(b) is an effective amount of at least one other anti-HIV active substance.

[17] A method for inhibiting HIV replication comprising administering the combination of (a) and (b) to a mammal, wherein
(a) is an effective amount of (S)-6-(3-Chloro-2-fluorobenzyl)-1-(1-hydroxymethyl-2-methylpropyl)-7-methoxy-4-oxo-1,4-dihydroquinoline-3-carboxylic acid or a pharmaceutically acceptable solvate or salt thereof, and
(b) is an effective amount of at least one other anti-HIV active substance.

[18] A method for treating a viral infection comprising administering the combination of (a) and (b) to a mammal, wherein
(a) is an effective amount of (S)-6-(3-Chloro-2-fluorobenzyl)-1-(1-hydroxymethyl-2-methylpropyl)-7-methoxy-4-oxo-1,4-dihydroquinoline-3-carboxylic acid or a pharmaceutically acceptable solvate or salt thereof, and
(b) is an effective amount of at least one other anti-HIV active substance.

[19] A method for treating a viral infection comprising administering the combination of (a) and (b) to a mammal, wherein
(a) is an effective amount of (S)-6-(3-Chloro-2-fluorobenzyl)-1-(1-hydroxymethyl-2-methylpropyl)-7-methoxy-4-oxo-1,4-dihydroquinoline-3-carboxylic acid or a pharmaceutically acceptable solvate or salt thereof, and
(b) is an effective amount of at least one other anti-HIV active substance, and
wherein the combination of (a) and (b) results in a synergistic effect for treating the viral infection.

[20] A kit comprising the combination of (a) and (b), wherein
(a) is an effective amount of (S)-6-(3-Chloro-2-fluorobenzyl)-1-(1-hydroxymethyl-2-methylpropyl)-7-methoxy-4-oxo-1,4-dihydroquinoline-3-carboxylic acid or a pharmaceutically acceptable solvate or salt thereof, and
(b) is an effective amount of at least one other anti-HIV active substance.

[21] A commercial package comprising the combination of (a) and (b), wherein
(a) is an effective amount of (S)-6-(3-Chloro-2-fluorobenzyl)-1-(1-hydroxymethyl-2-methylpropyl)-7-methoxy-4- oxo-1,4-dihydroquinoline-3-carboxylic acid or a pharmaceutically acceptable solvate or salt thereof, and
(b) is an effective amount of at least one other anti-HIV active substance,
and written matter associated therewith, the written matter stating that the combination of (a) and (b) can or should be used for treating an HIV infection.

[22] A commercial package comprising the combination of (a) and (b), wherein
(a) is an effective amount of (S)-6-(3-Chloro-2-fluorobenzyl)-1-(1-hydroxymethyl-2-methylpropyl)-7-methoxy-4-oxo-1,4-dihydroquinoline-3-carboxylic acid or a pharmaceutically acceptable solvate or salt thereof, and
(b) is an effective amount of at least one other anti-HIV active substance,
and written matter associated therewith, the written matter stating that the combination of (a) and (b) can or should be used for inhibiting integrase.

[23] A commercial package comprising the combination of (a) and (b), wherein
(a) is an effective amount of (S)-6-(3-Chloro-2-fluorobenzyl)-1-(1-hydroxymethyl-2-methylpropyl)-7-methoxy-4-oxo-1,4-dihydroquinoline-3-carboxylic acid or a pharmaceutically acceptable solvate or salt thereof, and
(b) is an effective amount of at least one other anti-HIV active substance, and written matter associated therewith, the written matter stating that the combination of (a) and (b) can or should be used for treatment of a viral infection.

[24] A method for inhibiting integrase in vitro, comprising adding the combination of (a) and (b) to a sample containing integrase, wherein
(a) is an effective amount of (S)-6-(3-Chloro-2-fluorobenzyl)-1-(1-hydroxymethyl-2-methylpropyl)-7-methoxy-4-oxo-1,4-dihydroquinoline-3-carboxylic acid or a pharmaceutically acceptable solvate or salt thereof, and
    (b) is an effective amount of at least one other anti-HIV active substance.

SEQUENCE LISTING FREE TEXT

Figure 1:
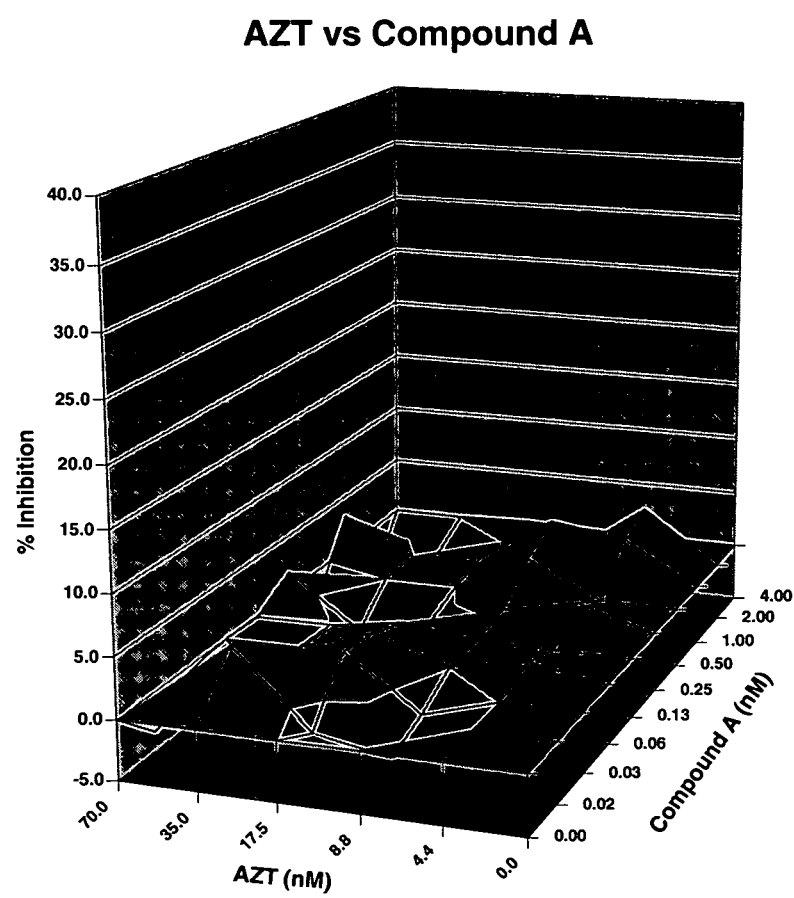
FIG. 1. Averaged 3-Dimensional Graph (n=3) for Drug Combination Assay of Compound A with AZT. Percent inhibition of viral-induced cell death versus independent concentrations of Compound A and AZT.

SEQ ID NO:1: Donor + chain for HIV integrase activity determination
SEQ ID NO:2: Donor − chain for HIV integrase activity determination
SEQ ID NO:3: Target + chain for HIV integrase activity determination
SEQ ID NO:4: Target − chain for HIV integrase activity determination

DETAILED DESCRIPTION OF THE INVENTION

I. Definitions

The term "isomers" includes, for example, E form and Z form present as geometric isomers, and when an asymmetric carbon atom exists, enantiomer and diastereomer are present as stereoisomers based thereon, and tautomer can be present. Compound A may have various isomers. Accordingly, the present invention encompasses all these isomers and mixtures thereof. The Compound A of the present invention may be isolated and purified from various isomers, byproducts, metabolites or prodrugs, where one having a purity of 90% or above may be isolated or one having a purity of 95% or above may be isolated.

A "pharmaceutically acceptable salt thereof" is any non-toxic salt formed from Compound A. For example, it can be obtained by reaction with: an inorganic acid such as hydrochloric acid, sulfuric acid, phosphoric acid, hydrobromic acid, and the like; an organic acid such as oxalic acid, malonic acid, citric acid, fumaric acid, lactic acid, malic acid, succinic acid, tartaric acid, acetic acid, trifluoroacetic acid, gluconic acid, ascorbic acid, methylsulfonic acid, benzylsulfonic acid, and the like; an inorganic base such as sodium hydroxide, potassium hydroxide, calcium hydroxide, magnesium hydroxide, ammonium hydroxide, and the like; an organic base such as methylamine, diethylamine, triethylamine, triethanolamine, ethylenediamine, tris(hydroxymethyl)methylamine, guanidine, choline, cinchonine, and the like; or an amino acid such as lysin, arginine, alanine, and the like. The present invention encompasses water-containing products and solvates, such as hydrates, of Compound A, and the like.

By the term "prodrug" is meant a derivative of Compound A of the present invention, which has a chemically or metabolically decomposable group and which, after administration to a body, restores to the original compound to show its inherent efficacy, including a complex and a salt free of covalent bond. The present invention also encompasses prodrugs and metabolites of each compound.

The prodrug is utilized, for example, for improving absorption by oral administration or targeting of a target site.

The chemically or metabolically decomposable group of the prodrug of Compound A may be added, for example, to a highly reactive functional group in Compound A, such as a hydroxyl group or a carboxyl group, and the like.

Examples of the hydroxyl-modifying group include acetyl group, propionyl group, isobutyryl group, pivaloyl group, benzoyl group, 4-methylbenzoyl group, dimethylcarbamoyl group, sulfo group, and the like. Examples of the carboxylmodifying group include ethyl group, pivaloyloxymethyl group, 1-(acetyloxy)ethyl group, 1-(ethoxycarbonyloxy) ethyl group, 1-(cyclohexyloxycarbonyloxy) ethyl group, carboxylmethyl group, (5-methyl-2-oxo-1,3-dioxol-4-yl)methyl group, phenyl group, o-tolyl group, and the like.

A "solvate" of Compound A, or a pharmaceutically acceptable salt of a compound of Compound A, has molecules of a suitable solvent incorporated in the crystal lattice. A suitable solvent is physiologically tolerable at the dosage administered. Examples of suitable solvents include ethanol, water, and the like. When water is the solvent, the molecule may also be referred to as a hydrate.

The term "therapeutically effective amount" or "effective amount" means an amount of Compound A, the at least one other anti-HIV agent, or combinations thereof that are effective in treating the named disorder or condition. An amount "effective to inhibit integrase" is an amount that yields a measurable decrease in viral integrase activity, as measured using an assay and end-point appropriate for that measurement. For instance, amounts effective to inhibit viral integrase for purposes of therapy are those amounts that, following administration, yield a detectable improvement in the symptoms associated with the given disease or condition under treatment. Where the viral integrase inhibition sought is in the context of an in vitro assay, for instance during screening of compounds for their ability to antagonize or promote activity of Compound A or combinations of Compound A with at least one other anti-HIV agent, then the viral integrase inhibition can most suitably be measured more directly as a decrease in virus-induced cytotoxicity.

The term "treat" or "treating" means to alleviate symptoms, eliminate the causation of the symptoms either on a temporary or permanent basis, or to prevent or slow the appearance of symptoms of the named disorder or condition. For example, in some embodiments of the present invention, "treating" refers to treating an HIV infection. In some embodiments, it means to prevent occurrence of a viral infection in an individual who has not yet been infected with the virus or exhibited symptoms of infection. For example, in one embodiment of the invention "treating" includes administration of the inventive combination to an individual who is at risk for potential exposure, or who has been exposed to a source of infection Examples of events with a potential risk for virus exposure include accidental needle stick, intravenous drug use, blood product transfusion, high risk sex, etc.

"Treating" also means, for example, administration of a pharmaceutical agent, including the combination of the present invention, to an individual who tested HIV positive but has not yet developed the disease state of AIDS, administration of a pharmaceutical agent to an individual who shows an improved disease state of AIDS after treatment, but who carries HIV still to be eradicated and whose relapse of AIDS is worried, and administration of a pharmaceutical agent before the infection of HIV out of a fear of possible infection.

II. Compound A

Compound A is (S)-6-(3-Chloro-2-fluorobenzyl)-1-(1-hydroxymethyl-2-methylpropyl)-7-methoxy-4-oxo-1,4-dihydroquinoline-3-carboxylic acid and has the following structural formula:

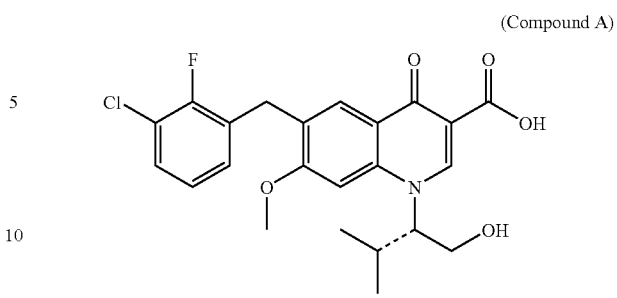
(Compound A)

The compound may also be used in the form of pharmaceutically acceptable solvates and salts thereof. Therapeutically useful embodiments of the present invention also encompass pharmaceutically acceptable isomers or prodrugs of Compound A. A method for synthesizing compound A is provided below in example 1. Other methods, or modifications of this example, would be readily apparent to one of ordinary skill in the art.

Compound A, and pharmaceutically acceptable solvates and salts thereof, are highly effective inhibitors of HIV integrase. Accordingly, Compound A is an effective anti-HIV agent useful for treating HIV infection, or for preventing or delaying the onset of symptoms associated with HIV infection and/or AIDS. Further, Compound A is effective at relatively low doses and exhibits very little cytotoxicity. Accordingly, the novel antiviral combinations of the present invention provide a means of treatment which may not only reduce the effective dose of either drug required for antiviral activity, thereby reducing cytotoxicity, but may also improve the absolute antiviral effect as a result of attacking the virus through multiple mechanisms. Similarly, the novel antiviral combinations provide a means for circumventing the development of viral resistance to a single therapy, thereby providing the clinician with a more efficacious treatment.

When used in combinations with other anti-HIV agents, Compound A can provide a combination therapy with fewer side effects for humans and/or with lower dose of compounds and/or with fewer times administration and/or with lower possibility of resistant strain appearing than existing therapies.

III. Other Anti-HIV Agents

Examples of the other anti-HIV agents and other anti-HIV active substance to be used for a multiple drug combination therapy include an anti-HIV antibody, an HIV vaccine, immunostimulants such as interferon, and the like, an HIV ribozyme, an HIV antisense drug, a reverse transcriptase inhibitor, a protease inhibitor, an inhibitor of bond between a bond receptor (CD4, CXCR4, CCR5, and the like) of a host cell recognized by virus and the virus, and the like.

As the other anti-HIV agents and other anti-HIV active substance to be used for a multiple drug combination therapy with the Compound A of the present invention, in some embodiments they are chosen from reverse transcriptase inhibitors and protease inhibitors. Two or three, or even a greater number of pharmaceutical agents can be used in combination, wherein a combination of pharmaceutical agents having different action mechanisms is one embodiment of the present invention. In addition, selection of pharmaceutical agents free of side effect duplication is another embodiment of the present invention.

Specific examples of HIV reverse transcriptase inhibitors include Retrovir® (zidovudine or AZT), Epivir® (lamivudine or 3TC), Zerit® (sanilvudine), Videx® (didanosine), Hivid® (zalcitabine), Ziagen® (abacavir sulfate), Viramune® (nevirapine), Stocrin® (efavirenz), Rescriptor® (delavirdine mesylate), Combivir® (zidovudine+lamivudine), Trizivir® (abacavir sulfate+lamivudine+zidovudine), Coactinon® (emivirine), Phosphonovir®, Coviracil®, alovudine (3'-fluoro-3'-deoxythymidine), Thiovir (thiophosphonoformic acid), Capravirin (5-[(3,5-dichlorophenyl)thio]-4-isopropyl-1-(4-pyridylmethyl)imidazole-2-methanol carbamic acid), Tenofovir (PMPA), Tenofovir disoproxil fumarate ((R)-[[2-(6-amino-9H-purin-9-yl)-1-methylethoxy]methyl] phosphonic acid bis(isopropoxycarbonyloxymethyl)ester fumarate), DPC-083 ((4S)-6-chloro-4-[(1E)-cyclopropylethenyl]-3,4-dihydro-4-trifluoromethyl-2 (1H)-quinazolinone), DPC-961 ((4S)-6-chloro-4-(cyclopropylethynyl)-3,4-dihydro-4-(trifluoromethyl)-2 (1H)-quinazolinone), DAPD ((−)-β-D-2,6-diaminopurine dioxolane), Immunocal, MSK-055, MSA-254, MSH-143, NV-01, TMC-120, DPC-817, GS-7340, TMC-125, SPD-754, D-A4FC, capravirine, UC-781, emtricitabine, alovudine, Phosphazid, UC-781, BCH-10618, DPC-083, Etravirine, BCH-13520, MIV-210, abacavir sulfate/lamivudine, GS-7340, GW-5634, GW-695634, and the like.

Specific examples of HIV protease inhibitors include Crixivan® (indinavir sulfate ethanolate), saquinavir, Invirase® (saquinavir mesylate), Norvir® (ritonavir), Viracept® (nelfinavir mesylate), lopinavir, Prozei® (amprenavir), Kaletra® (ritonavir+lopinavir), mozenavir dimesylate ([4R-(4α, 5α,6β)]-1-3-bis[(3-aminophenyl)methyl]hexahydro-5,6-dihydroxy-4,7-bis(phenylmethyl)-2H-1,3-diazepin-2-one dimethanesulfonate), tipranavir (3'-[(1R)-1-[(6R)-5,6-dihydro-4-hydroxy-2-oxo-6-phenylethyl-6-propyl-2H-pyran-3-yl]propyl]-5-(trifluoromethyl)-2-pyridinesulfonamide), lasinavir (N-[5(S)-(tert-butoxycarbonylamino)-4(S)-hydroxy-6-phenyl-2(R)-(2,3,4-trimethoxybenzyl)hexanoyl]-L-valine 2-methoxyethylenamide), KNI-272 ((R)—N-tert-butyl-3-[(2S,3S)-2-hydroxy-3-N—[(R)-2-N-(isoquinolin-5-yloxyacetyl)amino-3-methylthiopropanoyl]amino-4-phenylbutanoyl]-5,5-dimethyl-1,3-thiazolidine-4-carboxamide), GW-433908, TMC-126, DPC-681, buckminsterfullerene, MK-944A (MK944 (N-(2(R)-hydroxy-1(S)-indanyl)-2(R)-phenylmethyl-4(S)-hydroxy-5-[4-(2-benzo[b]furanylmethyl)-2(S)-(tert-butylcarbamoyl)piperazin-1-yl]pentanamide)+indinavir sulfate), JE-2147 ([2(S)-oxo-4-phenylmethyl-3(S)-[(2-methyl-3-oxy)phenylcarbonylamino]-1-oxabutyl]-4-[(2-methylphenyl)methylamino]carbonyl-4(R)-5,5-dimethyl-1,3-thiazole), BMS-232632 ((3S,8S,9S,12S)-3,12-bis(1,1-dimethylethyl)-8-hydroxy-4,11-dioxo-9-(phenylmethyl)-6-[[4-(2-pyridinyl)phenyl]methyl]-2,5,6,10,13-pentaazatetradecanedicarboxylic acid dimethyl ester), DMP-850 ((4R,5S,6S,7R)-1-(3-amino-1H-indazol-5-ylmethyl)-4,7-dibenzyl-3-butyl-5,6-dihydroxyperhydro-1,3-diazepin-2-one), DMP-851, RO-0334649, Nar-DG-35, R-944, VX-385, TMC-114, Tipranavir, Fosamprenavir sodium, Fosamprenavir calcium, Darunavir, GW-0385, R-944, RO-033-4649, AG-1859, and the like.

The HIV integrase inhibitor may be S-1360, L-870810, and the like. The DNA polymerase inhibitor or DNA synthesis inhibitor may be Foscavir®, ACH-126443 (L-2',3'-didehydro-dideoxy-5-fluorocytidine), entecavir ((1S,3S,4S)-9-[4-hydroxy-3-(hydroxymethyl)-2-methylenecyclopentyl] guanine), calanolide A ([10R-(10α,11β,12α)]-11,12-dihydro-12-hydroxy-6,6,10,11-tetramethyl-4-propyl-2H, 6H,10H-benzo[1,2-b:3,4-b':5,6-b"]tripyran-2-one), calanolide B, NSC-674447 (1,1'-azobisformamide), Iscador (viscum alubm extract), Rubutecan, and the like. The HIV antisense drug may be HGTV-43, GEM-92, and the like. The anti-HIV antibody or other antibody may be NM-01, PRO-367, KD-247, Cytolin®, TNX-355 (CD4 antibody), AGT-1, PRO-140 (CCR5 antibody), Anti-CTLA-4 Mab, and the like. The HIV vaccine or other vaccine may be ALVAC®, AIDS-VAX®, Remune®, HIV gp41 vaccine, HIV gp120 vaccine, HIV gp140 vaccine, HIV gp160 vaccine, HIV p17 vaccine, HIV p24 vaccine, HIV p55 vaccine, AlphaVax Vector System, canarypox gp160 vaccine, AntiTat, MVA-F6 Nef vaccine, HIV rev vaccine, C4-V3 peptide, p2249f, VIR-201, HGP-30W, TBC-3B, PARTICLE-3B, and the like, Antiferon (interferon-α vaccine), and the like.

The interferon or interferon agonist may be Sumiferon®, MultiFeron®, interferon-τ, Reticulose, Human leukocyte interferon alpha, and the like. The CCR5 antagonist may be SCH-351125, and the like. The pharmaceutical agent acting on HIV p24 may be GPG-NH2 (glycyl-prolyl-glycinamide), and the like. The HIV fusion inhibitor may be FP-21399 (1,4-bis[3-[(2,4-dichlorophenyl)carbonylamino]-2-oxo-5,8-disodium sulfonyl]naphthyl-2,5-dimethoxyphenyl-1,4-dihydrazone), T-1249, Synthetic Polymeric Construction No 3, pentafuside, FP-21399, PRO-542, Enfuvirtide, and the like. The IL-2 agonist or antagonist may be interleukin-2, Imunace®, Proleukin®, Multikine®, Ontak®, and the like. The TNF-α antagonist may be Thalomid® (thalidomide), Remicade® (infliximab), curdlan sulfate, and the like. The α-glucosidase inhibitor may be Bucast®, and the like.

The purine nucleoside phosphorylase inhibitor may be peldesine (2-amino-4-oxo-3H,5H-7-[(3-pyridyl)methyl]pyrrolo[3,2-d]pyrimidine), and the like. The apoptosis agonist or inhibitor may be Arkin Z®, Panavir®, Coenzyme Q10 (2-deca(3-methyl-2-butenylene)-5,6-dimethoxy-3-methyl-p-benzoquinone), and the like. The cholinesterase inhibitor may be Cognex®, and the like, and the immunomodulator may be Imunox®, Prokine®, Met-enkephalin (6-de-L-arginine-7-de-L-arginine-8-de-L-valinamide-adrenorphin), WF-10 (10-fold dilute tetrachlorodecaoxide solution), Perthon, PRO-542, SCH-D, UK-427857, AMD-070, AK-602, and the like.

In addition, Neurotropin®, Lidakol®, Ancer 20®, Ampligen®, Anticort®, Inactivin®, and the like, PRO-2000, Rev M10 gene, HIV specific cytotoxic T cell (CTL immunotherapy, ACTG protocol 080 therapy, CD4-ζ gene therapy), SCA binding protein, RBC-CD4 complex, Motexafin gadolinium, GEM-92, CNI-1493, (±)—FTC, Ushercell, D2S, BufferGel®, VivaGel®, Glyminox vaginal gel, sodium lauryl sulfate, 2F5, 2F5/2G12, VRX-496, Ad5gag2, BG-777, IGIV-C, BILR-255, and the like may be used in the combination therapy.

IV. Methods of Treatment

Combinations of Compound A with at least one other anti-HIV agent of the present invention can be administered to a mammal (human, mouse, rat, hamster, rabbit, cat, dog, bovine, sheep, swine, and the like) as an anti-HIV agent, an integrase inhibitor, an antiviral agent, and the like.

An anti-HIV agent is generally required to sustain its effect for a long time, so that can be effective not only for temporal suppression of viral growth but also for prohibition of viral re-growth. This means that a long term administration is necessary and that a high single dose may be frequently inevitable to sustain effect for a longer period through the night. Such long term and high dose administration increases the risk of causing side effects.

In view of this, one of the embodiments of the combination of the present invention is a combination comprising compounds permitting high absorption by oral administration, and such compounds capable of maintaining blood concentration of the administered compound for an extended period of time.

Specific combination of pharmaceutical agents include a combination of a group consisting of Efavirenz, Tenofovir, Emtricitabine, Indinavir, Nelfinavir, Atanazavir, Ritonavir+Indinavir, Ritonavir+Lopinavir, Ritonavir+Saquinavir, Didanosine+Lamivudine, Zidovudine+Didanosine, Stavudine+Didanosine, Zidovudine+Lamivudine, Stavudine+Lamivudine, and Emtriva and the Compound A of the present invention (Combinations are discussed further in Guidelines for the Use of Antiretroviral Agents in HIV-Infected Adults and Adolescents. Aug. 13, 2001). One embodiment includes two drug therapy by the combination of Compound A with Efavirenz, Indinavir, Nelfinavir, Tenofovir, Emtricitabine, Zidovudine, or Lamivudine. Another embodiment includes three drug therapy by the combination of Compound A with Zidovudine+Lamivudine, Tenofovir+Lamivudine, Tenofovir+Zidovudine, Tenofovir+Efavirenz, Tenofovir+Nelfinavir, Tenofovir+Indinavir, Tenofovir+Emtricitabine, Emtricitabine+Lamivudine, Emtricitabine+Zidovudine, Emtricitabine+Efavirenz, Emtricitabine+Nelfinavir, Emtricitabine+Indinavir, Nelfinavir+Lamivudine, Nelfinavir+Zidovudine, Nelfinavir+Efavirenz, Nelfinavir+Indinavir, Efavirenz+Lamivudine, Efavirenz+Zidovudine, or Efavirenz+Indinavir.

While the dose varies depending on age, body weight, symptom, treatment effect, administration method, and the like, Compound A is generally administered at about 0.01 mg to about 1 g per administration for an adult, which is given once to several times a day orally or in a dosage form of an injection such as intravenous injection, and the like. The effective dosage of each at least one other anti-HIV active substance for use in the present inventive combination is readily available in published sources to one of ordinary skill in the art. The present invention contemplates the use of the clinically intended effective dosage schedules for each other anti-HIV active substance.

For further example, oral dosages of Compound A for combination therapy may be any dosage ranging from about 0.005 mg to about 1000 mg per administration. For example, single administrations of Compound A in the combination therapy may be 0.01 mg, 0.05 mg, 0.1 mg, 0.5 mg, 1.0 mg, 2 mg, 5 mg, 10 mg, 15 mg, 20 mg, 50 mg, 100 mg, 200 mg, 300 mg, 400 mg, 500 mg, 600 mg, 700 mg, 800 mg, 9000 mg, or 1000 mg, per administration.

For zidovudine (AZT), for example, a recommended oral dose of zidovudine for adults for treating HIV infection is 100 mg every 4 hours. Also for example, a standard intravenous of zidovudine dose is about 1 to about 2 mg/kg every 4 hours. For children 3 months to 12 years old, the oral starting dose is 180 mg/m2 every 6 hours not to exceed 200 mg every 6 hours. Infants should be given 2 mg/kg orally every 6 hours within 12 hours of birth and for 6 weeks or 1.5 mg/kg intravenously every 6 hours. To prevent HIV transmission from mother to fetus, the dose is 100 mg five times daily or 200 mg three times daily. Treatment should be initiated between the 14th and 34th weeks of pregnancy and continued until the time of labor. During labor and delivery, 2 mg/kg should be administered intravenously over 1 hr followed by 1 mg/kg/hr until the umbilical cord is clamped.

For lamivudine (3TC), for example, a recommended oral dose of lamivudine for adults for treating HIV infection is 150 mg twice daily for those weighing 50 kg or more and 2 mg/kg twice daily if less than 50 kg. Children (12 to 16 years old) weighing 50 kg or more should receive 150 mg twice daily. Children (3 months to 12 years old) should be treated with 4 mg/kg twice daily up to a maximum dose of 300 mg daily. For postexposure prevention of HIV infection, 150 mg twice daily of lamivudine is administered in conjunction with 600 mg daily of zidovudine (Retrovir) for 28 days.

For the combination of lamivudine/zidovudine (3TC/AZT), for example, the combination is available as tablets of 150 mg/300 mg (3TC/AZT) and for treating HIV infection the recommended oral dose for adults or children greater than 12 years of age is one tablet twice daily.

For efavirenz, for example, a recommended oral dose for adults for treating HIV infection is 600 mg daily. For tenofovir disoproxil fumarate, for example, a recommended oral dose for adults for treating HIV infection is 300 mg daily. Each tablet contains 300 mg of tenofovir disoproxil fumarate, which is equivalent to 245 mg of tenofovir disoproxil. For indinavir, for example, a recommended oral dose for adults for treating HIV infection is 800 mg every eight hours. For nelfinavir, for example, a recommended dose for adults is 1250 mg twice daily or 750 mg three times daily. The recommended dose for children 2-13 years of age is 20-30 mg/kg three times daily.

Other anti-HIV agents may be administered at doses consistent with the recognized recommended administration schedules. Examples of such dosages may be any dosage ranging from 20 mg to 2000 mg per administration. For example, single administrations of the at least one other anti-HIV agent may be 20 mg, 50 mg, 100 mg, 200 mg, 300 mg, 400 mg, 500 mg, 600 mg, 700 mg, 800 mg, 9000 mg, 1000 mg, 1200 mg, 1400 mg, 1600 mg, 1800 mg, or 2000 mg per administration.

An embodiment of the present invention also contemplates the use of doses for each other anti-HIV active substance that are below the clinically intended effective dosage schedules for each other anti-HIV active substance. In some embodiments of the present invention, the beneficial effects and efficacy of the present inventive combination may optionally permit administration of effective doses of each other anti-HIV active substance that are lower than the clinically intended effective dosage or the recommended dosage. For example, an embodiment of the present invention contemplates the use of doses for each other anti-HIV active substance that range from, for example, 5% to 99%, such as 5%, 10%, 20%, 30%, 50%, 75%, or 90%, of the lowest clinically intended effective dosage for each other anti-HIV active substance.

When a combination of Compound A with at least one other anti-HIV agent of the present invention is used as a pharmaceutical preparation, it is admixed with pharmaceutically acceptable carriers, excipients, diluents, extending agents, disintegrants, stabilizers, preservatives, buffers, emulsifiers, flavoring agents, coloring agents, sweetening agents, thickeners, correctives, dissolution aids, other additives, and the like, that are generally known including water, vegetable oil, alcohol (e.g., ethanol or benzyl alcohol, and the like), polyethylene glycol, glycerol triacetate, gelatin, carbohydrate (e.g., lactose, starch, and the like.), magnesium stearate, talc, lanolin, petrolatum, and the like, formed into tablet, pill, powder, granule, suppository, injection, eye drop, liquid, capsule, troche, aerosol, elixir, suspension, emulsion, syrup, and the like, by a conventional method, and administered systemically or topically, and orally or parenterally.

An embodiment of the present inventive method provides for the administration to a mammal, such as a human, monkey, cat, and the like, of an effective amount of Compound A and at least one other anti-HIV agent. The administration may be accomplished by co-administration of at least two of the anti-HIV agents, i.e., administering Compound A and a retroviral protease inhibitor such that an effective amount of both agents are present in said mammal at any one time. Alternatively, the administration may be accomplished by sequential or alternating administration of Compound A and at least one other anti-HIV agent, i.e. administering Compound A and one other anti-HIV agent such that an effective amount of only Compound A or only the other anti-HIV agent is present in said mammal at any one time. With the proper selection of the at least one other anti-HIV agent, this method can effectively control the propagation of the retrovirus even in the presence of resistant strains to any one of the other anti-HIV agents.

The combination of Compound A and at least one other anti-HIV agent of the present invention can be formulated as separate compositions which are given at substantially the same time. Or, the combination of Compound A and at least one other anti-HIV agent of the present invention can be formulated as a single composition such that all of the active agents are administered at a therapeutically effective amount to the host in each dose. Alternatively, Compound A and the at least one other anti-HIV agent of the present invention can be administered to the host at different times such that only one or two active agents at a time are at a therapeutically effective amount in the host. Accordingly, Compound A and the other anti-HIV agent agents of the present invention can be administered to an individual either sequentially or simultaneously. The combination of the present invention may be administered as a single dose daily or as multiple doses daily, wherein each dose comprises Compound A, at least one other anti-HIV agent, or both. In some embodiments of the present invention, the administration of a dose of Compound A, at least one other anti-HIV agent, or both may occur continuously over any therapeutically effective length of time, such as, for example, when using an intravenous drip, a skin patch, a subdermal pump, a polymeric implant; or administration of a nanosphere formulation.

The combinations and methods of the present invention are also effective in preventing the growth of retroviruses in an in vitro solution. Human, animal, and microbial cell cultures, such as T-lymphocyte cultures, are utilized for a variety of well known purposes, such as research and diagnostic procedures including calibrators and controls. Prior to and during the growth and storage of a cell culture, the subject compounds may be added to the cell culture medium at an effective concentration to prevent the unexpected or undesired replication of a retrovirus that may inadvertently or unknowingly be present in the cell culture. The virus may be present originally in the cell culture, for example HIV is known to be present in human T-lymphocytes long before it is detectable in blood, or through exposure to the virus. This use of the subject combinations and methods prevent the unknowing or inadvertent exposure of a potentially lethal retrovirus to a researcher or clinician.

Further, the combinations and methods of the present invention are also effective as an in vitro screening method for identifying additional anti-HIV agents that may be beneficial for combination therapy with Compound A for treating HIV infections. For example, a test compound may be added to an HIV infected cell culture in combination with Compound A or Compound A plus at least one other known anti-HIV agent and the replication of the retrovirus in the cell culture is measured and compared to control samples, e.g. samples not containing the test compound, samples containing only test compound, or other variants thereof. Comparison of the results, for example, will indicate test compounds that may be beneficially used in combination therapy with Compound A or Compound A plus at least one other known anti-HIV agent. In some embodiments, particularly beneficial test compounds will be identified by their synergistic results when they are used in combination with Compound A or Compound A plus at least one other known anti-HIV agent.

Industrial Field of Utilization

The combinations of the present invention have high HIV inhibitory activity with relatively low cytotoxocity.

Therefore, in an embodiment, the combinations of the present invention can be useful for the prevention or treatment of AIDS, as anti-HIV agents having HIV integrase inhibitory activity. Moreover, in another embodiment, the combinations of the present invention can further be combined with other anti-HIV agents such as protease inhibitors, reverse transcriptase inhibitors, and the like. Thus, the compounds can become more effective anti-HIV agents and may provide synergistic results from the combined use of the anti-HIV agents with Compound A. Since Compound A has high inhibitory activity specific for integrases, combinations comprising Compound A can provide a safe pharmaceutical agent for combination therapies in humans with few side effects and efficacious treatment results.

Further non-limiting examples of the present invention follow.

EXAMPLES

Example 1

Synthesis of Compound A

An example of the production method of Compound A of the present invention is shown in the following. However, the production method of Compound A of the present invention is not limited to this example. Other methods would be readily apparent to one of ordinary skill in the art.

Even in the absence of description in the production method, efficient production can be afforded, where necessary, by introducing a protecting group into a functional group followed by deprotection in a subsequent step, by using a compound with a functional group as a precursor in each step and converting the group to a desired functional group in a suitable step, by exchanging the order of respective production methods and steps, or by other method.

The workup in each step can be applied by a typical method, wherein isolation and purification is performed by selecting or combining conventional methods as necessary, such as crystallization, recrystallization, distillation, partitioning, silica gel chromatography, preparative HPLC, and the like.

A. Step 1

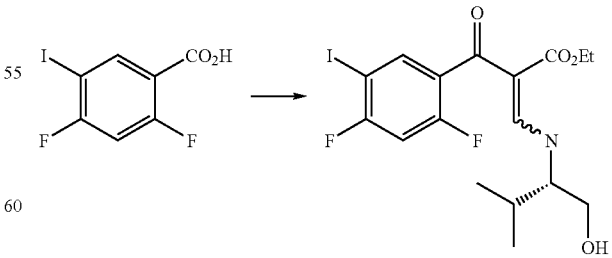

2,4-Difluoro-5-iodobenzoic acid (650.57 g, 2.29 mol) was dissolved in toluene (1300 ml), and thionyl chloride (184 ml, 2.52 mol) and dimethylformamide (catalytic amount) were added. The mixture was stirred at 90° C. for 2 hrs. After allowing the mixture to cool, the reaction solution was concentrated under reduced pressure. The residue was dissolved in toluene (330 ml) followed by concentration under reduced pressure, and repeated again. The residue was dissolved in toluene (690 ml) and the obtained solution was added dropwise to a solution of ethyl 3,3-dimethylaminoacrylate (361.52 g, 2.525 mol) and diisopropylethylamine (480 ml, 2.75 mol) in toluene (690 ml) and the mixture was stirred with heating at 90° C. for 3 hrs. After allowing the mixture to cool, (S)-(+)-valinol (260.00 g, 2.52 mol) was added to the reaction mixture and the mixture was stirred at room temperature for 1 hr. Water (2600 ml) was added to the reaction mixture and the mixture was partitioned. The aqueous layer was extracted with toluene (680 ml). The organic layers were combined, washed twice with water (2000 ml), and dried over sodium sulfate. After filtration, concentration under reduced pressure gave a crude substance (1180 g) as a brown oil.

B. Step 2

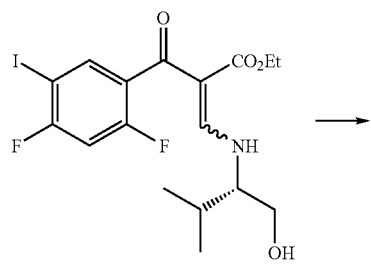

The crude product (1180 g) obtained in Step 1 was dissolved in dimethylformamide (2500 ml) and finely ground potassium carbonate (292.00 g, 1.06 mol) was added. The mixture was stirred at room temperature for 22 hrs. The reaction mixture was added to ice water (ca. 10 L) and the mixture was stirred for 30 min. The precipitate was collected by filtration and washed with water (2000 ml). The solid was vacuum-dried, and suspended in ethyl acetate (5000 ml). Filtration and vacuum-drying gave an object product (774.63 g, yield 82%) as a white yellow solid.

$^1$H NMR (DMSO-$d_6$ 300 MHz) (δ) ppm: 0.72 (3H, d, J=6.6 Hz), 1.10 (3H, d, J=6.6 Hz), 1.28 (3H, t, J=7.0 Hz), 2.27 (1H, br), 3.77 (1H, br), 3.86 (1H, br), 4.23 (2H, q, J=7.0 Hz), 4.56 (1H, br), 5.12 (1H, t, J=4.9 Hz), 8.09 (1H, d, J=11.1 Hz), 8.62 (1H, d, J=7.5 Hz), 8.68 (1H, s)

MS (ESI): M+ 448

C. Step 3

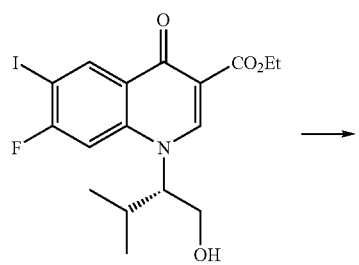

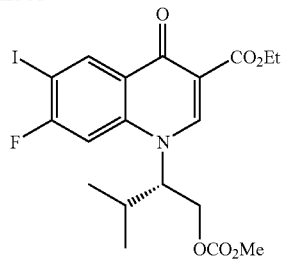

The compound (626.15 g, 1.40 mol) obtained in Step 2 was dissolved in chloroform (1250 ml), and pyridine (433 ml, 5.60 mol) and 4-(dimethylamino)pyridine (17.10 g, 0.14 mol) were added. A solution of methyl chloroformate (529.30 g, 5.60 mol) in chloroform (1250 ml) was added dropwise at less than 10° C.

After completion of the addition, the mixture was stirred at the same temperature for 30 min. The reaction mixture was washed successively with water (1250 ml), 2N hydrochloric acid (1250 ml), water (630 ml) and saturated aqueous sodium hydrogen carbonate (630 ml), and dried over sodium sulfate. After filtration, the residue was concentrated under reduced pressure to give a crude substance (834.02 g) as a brown oil.

D. Step 4

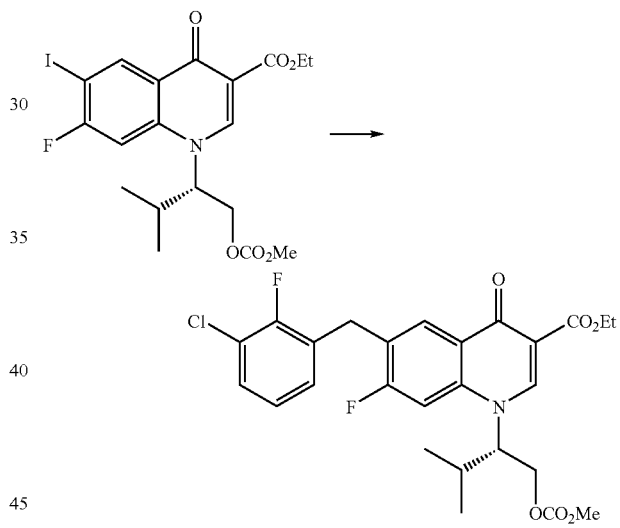

Preparation of 3-chloro-2-fluorobenzylzinc bromide tetrahydrofuran solution

Under an argon stream, zinc powder (113.02 g, 1.73 mol) was suspended in tetrahydrofuran (350 ml), and 1,2-dibromoethane is (1.207 ml, 14.00 mmol) and trimethylsilyl chloride (8.88 ml, 70.00 mmol) were added at 60° C. The mixture was stirred with heating at 30 min. A solution of 3-chloro-2-fluorobenzyl bromide (406.73 g, 1.82 mol) in tetrahydrofuran (700 ml) was added dropwise at 60° C. The mixture was stirred with heating for 1 hr to give a solution of 3-chloro-2-fluorobenzylzinc bromide.

The crude product (834.02 g) obtained in Step 3 was dissolved in tetrahydrofuran (1060 ml), and dichlorobis(triphenylphosphine)palladium(II) (19.65 g, 28.00 mmol) was added under an argon stream and a solution of 3-chloro-2-fluorobenzylzinc bromide (1.82 ml) was added dropwise at 60° C. After completion of the addition, the mixture was heated under reflux for 1.5 hrs. After allowing the mixture to cool, toluene (2120 ml) and 20% aqueous ammonium chloride solution (1410 ml) were added to the reaction solution, and the mixture was stirred and partitioned. The organic layer was washed twice with 20% aqueous ammonium chloride solution (710 ml) and twice with saturated aqueous sodium hydrogen carbonate (710 ml) and dried over magnesium sulfate. After filtration, the filtrate was concentrated under reduced pressure to give a crude substance (849.34 g) as a brown oil.

E. Step 5

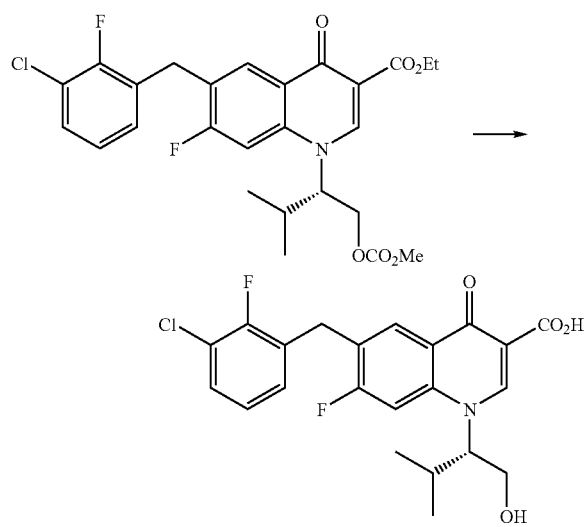

The crude product (849.34 g) obtained in Step 4 was dissolved in isopropanol (1100 ml) and 4N aqueous sodium hydroxide solution (1050 ml, 4.20 mmol) was added. The mixture was stirred with heating at 50° C. for 1.5 hrs. Activated carbon (37 g) was added to the reaction solution and the mixture was stirred at room temperature for 30 min. The mixture was filtered through Celite and 6N hydrochloric acid (740 ml) and ethyl acetate (3650 ml) were added to the filtrate. The mixture was stirred and partitioned. The organic layer was concentrated under reduced pressure and the residue was suspended in isopropanol (1070 ml). The mixture was stirred at 60° C. for 1 hr. After allowing the mixture to cool, the solid was collected by filtration. The solid was washed with isopropanol (740 ml) and vacuum-dried to give a product (446.51 g, yield 73%) as a pale-yellow solid.

$^1$H NMR (DMSO-$d_6$ 400 MHz) (δ) ppm: 0.71 (3H, d, J=6.5 Hz), 1.13 (3H, d, J=6.5 Hz), 2.36 (1H, br), 3.77 (1H, br), 3.94 (1H, br), 4.25 (2H, s), 4.77 (1H, br), 5.16 (1H, t, J=2.4 Hz), 7.19-7.23 (1H, m), 7.32-7.35 (1H, m), 7.48-7.52 (1H, m), 8.24-8.28 (2H, m), 9.00 (1H, s), 15.00 (1H, s)

MS (ESI): M+ 436

F. Step 6

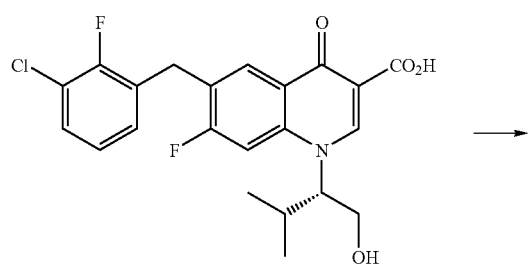

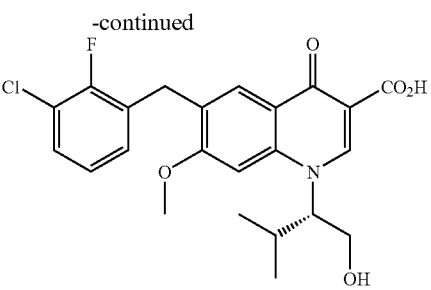

The compound (443.59 g, 1.02 mol) obtained in Step 5 was dissolved in methanol (2400 ml), and a 28% sodium methoxide in methanol (2077 ml, 10.17 mol) and water (44.30 ml, 2.46 mol) were added. The mixture was heated under reflux for 17.5 hrs. Activated carbon (22 g) was added to the reaction solution and the mixture was stirred at room temperature for 1 hr. The mixture was filtered through Celite and the filtrate was concentrated under reduced pressure. Water (1770 ml) was added to the residue and the mixture was stirred with ice-cooling for 1 hr. Then, 6N hydrochloric acid (1790 ml) was further added and the mixture was stirred at room temperature for 2 hrs. Ethyl acetate (1770 ml) was added and to the mixture was stirred and partitioned. The organic layer was washed twice with 10% brine (890 ml), and dried over sodium sulfate. After filtration, the filtrate was concentrated under reduced pressure, and a part of the residue was recrystallized several times (final recrystallization solvent was methanol-water) to give an object product (28.60 g, yield 67%) as a white solid.

$^1$H NMR (DMSO-$d_6$ 400 MHz) (δ) ppm: 0.72 (3H, d, J=6.5 Hz), 1.16 (3H, d, J=6.5 Hz), 2.30-2.50 (1H, m), 3.70-3.90 (1H, m), 3.90-4.00 (1H, m), 4.03 (3H, s), 4.12 (2H, s), 4.80-4.90 (1H, m), 5.19 (1H, t, J=5.2 Hz), 7.19-7.25 (2H, m), 7.46-7.51 (2H, m), 8.04 (1H, s), 8.88 (1H, s), 15.44 (1H, s)

MS (ESI): M+ 448.

The compound obtained was (S)-6-(3-Chloro-2-fluorobenzyl)-1-(1-hydroxymethyl-2-methylpropyl)-7-methoxy-4-oxo-1,4-dihydroquinoline-3-carboxylic acid ("Compound A") and has the following structural formula:

(Compound A)

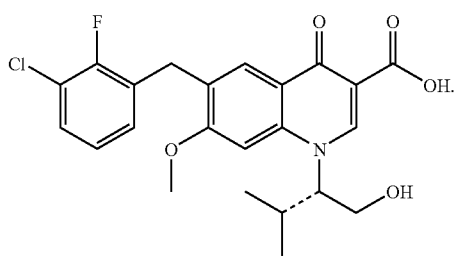

Example 2

Production of Integrase Protein

The following explains evaluation methods of the HIV integrase inhibitory activity of Compound A of the present invention.

(i) Construction of Recombinant Integrase Gene Expression System

The 185th phenylalanine of HIV integrase full length gene (J. Virol., 67, 425-437 (1993)) was substituted by histidine and inserted into the restriction enzyme NdeI and XhoI sites of plasmid pET21a(+) (Novagen), whereby an integrase expression vector pET21a-IN-F185H was constructed.

(ii) Production and Purification of Integrase Protein

*Escherichia coli* recombinant BL21(DE3) transformed with plasmid pET21a-IN-F185H obtained in (i) was shake cultured at 30° C. in a liquid medium containing ampicillin. When the culture reached the logarithmic growth phase, isopropyl-β-D-thiogalactopyranoside was added to promote expression of integrase gene. The culture was continued for 3 hrs to promote accumulation of the integrase protein. The recombinant *E. coli* was collected in pellets by centrifugal separation and preserved at −80° C.

The *E. coli* was suspended in Lysis buffer (20 mM HEPES (pH 7.5), 5 mM DTT, 10 mM CHAPS, 10% glycerol) containing 1M sodium chloride and subjected to repeat pressurization and depressurization for rupture, and centrifugal separation at 4° C., 40,000×g, 60 min to recover a water-soluble fraction (supernatant). This was diluted 10-fold with Lysis buffer free of sodium chloride, mixed with SP-Sepharose (Pharmacia Corporation) and stirred at 4° C. for 60 min to allow adsorption of integrase protein to the resin. The resin was washed with Lysis buffer containing 100 mM sodium chloride and the integrase protein was eluted with Lysis buffer containing 1M sodium chloride.

The eluted integrase protein solution was applied to a Superdex 75 (Pharmacia Corporation) column for gel filtration. The protein was eluted with Lysis buffer containing 1M sodium chloride.

The obtained fractions of the integrase protein were collected and preserved at −80° C.

(iii) Preparation of DNA Solution

The following DNA (synthesized using the method of Greiner) was dissolved in TE buffer (10 mM Tris-hydrochloric acid (pH 8.0), 1 mM EDTA) and mixed with donor DNA, target DNA, each complementary strand (+ and − strands) to 1 µM. The mixture was heated at 95° C. for 5 min, 80° C. for 10 min, 70° C. for 10 min, 60° C. for 10 min, 50° C. for 10 min and 40° C. for 10 min and preserved at 25° C. to give a double stranded DNA, which was used for the test.

Donor DNA (− strand having biotin attached to the 5' terminal)

Donor + strand: 5'-Biotin-ACC CTT TTA GTC AGT GTG GAA AAT CTC TAG CA-3' (SEQ ID NO:1)

Donor − strand: 5'-ACT GCT AGA GAT TTT CCA CAC TGA CTA AAA G-3' (SEQ ID NO:2)

Target DNA (+, − strands both having digoxigenin added at 3' terminal)

Target + strand: 5'-TGA CCA AGG GCT AAT TCA CT-Dig-3' (SEQ ID NO:3)

Target − strand: 5'-AGT GAA TTA GCC CTT GGT CA-Dig-3' (SEQ ID NO:4)

Example 3

Determination of In Vitro HIV Integrase Inhibitory Activity

The donor DNA was diluted with TE buffer to 10 nM, of which 50 µl was added to each well of streptavidin-coated microtiter plate (Roche) and allowed to adsorb at 37° C. for 60 min. The DNA was washed with phosphate buffer (Dulbecco PBS, Sanko Junyaku Co., Ltd.) containing 0.1% Tween 20 and phosphate buffer. Then, a reaction mixture (70 µl) having the following composition, Compound A (10 µl) diluted with the reaction mixture and 100 µg/ml integrase protein (10 µl) were added to each well and reacted at 37° C. for 60 min.

Then, 50 nM target DNA (10 µl) was added, reacted at 37° C. for 10 min and washed with phosphate buffer containing 0.1% Tween 20 to stop the reaction.

Then, 100 mU/ml peroxidase labeled anti-digoxigenin antibody solution (Roche, 100 µl) was added, and the mixture was reacted at 37° C. for 60 min, followed by washing with phosphate buffer containing 0.1% Tween 20.

A peroxidase color solution (Bio Rad, 100 µl) was added and allowed to react at room temperature for 4 min. The color reaction was stopped by adding 1N sulfuric acid (100 µl). The absorbance at 450 nm was measured.

The HIV integrase inhibitory activity ($IC_{50}$) of Compound A of the present invention was calculated from the inhibition rate according to the following formula.

Inhibition rate (%)=[1−(Test Sample—Blank)/(Control—Blank)]×100.

Test Sample=absorbance of well in the presence of test compound.

Control=absorbance of well in the absence of test compound.

Blank=absorbance of well in the absence of test compound, in the absence of integrase protein.

Compound A resulted in an enzyme $IC_{50}$ value of 0.0029 µM.

Example 4

Evaluation of In Vitro Antiviral Activity

The effect of combined use of Compound A of the present invention with known anti-HIV agents has been determined as shown below.

For example, the anti-HIV-1 activity of Compound A in combination with a variety of known anti-HIV inhibitors (AZT, 3TC, PMPA, efavirenz, indinavir, nelfinavir, AZT/3TC, and PMPA/3TC) was measured. This work was performed using the Prichard and Shipman MacSynergy II three-dimensional model for statistical evaluation of combination anti-HIV assays. Using a standard microtiter plate format, each combination assay was performed in CEM-SS T-lymphocytic cells acutely infected with the a laboratory-adapted strain, HIV-1$_{IIIB}$, and viral growth/inhibition was evaluated by measuring by monitoring virus-induced cytopathic effects (CPE) at the experimental endpoint.

A. Drug Preparation

A 20 mM stock solution of Compound A was prepared using DMSO as the diluent. Compound A was tested at a 4 nM high-test concentration with 8 additional serial 1:2 dilutions. Other anti-HIV agents (AZT, 3TC, PMPA, efavirenz, indinavir, nelfinavir, AZT/3TC, and PMPA/3TC) were supplied by Southern Research Institute (Frederick, Md. 21701). AZT was dissolved in sterile $dH_2O$ and the remainder of the control compounds were dissolved in DMSO for analysis in the combination assays. AZT/3TC were mixed at a ratio of 0.025 µM/0.25 µM (1:10) and PMPA/3TC at a ratio of 12.5 µM/0.25 µM (50:1). In all cases the final DMSO concentration was <0.25%, which has been previously shown to have no effect in the described assays.

B. Efficacy Evaluation in CEM-SS Cells

1. Anti-HIV-1 Cytoprotection Assay a. Cell Preparation

CEM-SS cells were passaged in T-75 flasks prior to use in the antiviral assay. On the day preceding the assay, the cells were split 1:2 to assure they were in an exponential growth phase at the time of infection. Total cell and viability quantification was performed using a hemacytometer and trypan blue exclusion. Cell viability was greater than 95% for the cells to be utilized in the assay. The cells were resuspended at $5\times10^4$ cells/ml in tissue culture medium (RPMI 1640 supplemented with 10% FBS) and added to the drug-containing microtiter plates in a volume of 50 µl.

b. Virus Preparation

The virus used for these tests was the lymphocytropic virus strain HIV-1$_{IIIB}$. This virus was obtained from the NIH AIDS Research and Reference Reagent Program and was grown in CEM-SS cells for the production of stock virus pools. For each assay, a pre-titered aliquot of virus was removed from the freezer (−80° C.) and allowed to thaw slowly to room temperature in a biological safety cabinet. The virus was resuspended and diluted into tissue culture medium such that the amount of virus added to each well in a volume of 50 µl was the amount determined to give between 85 to 95% cell killing at 6 days post-infection. TCID$_{50}$ calculations by endpoint titration in CEM-SS cells indicated that the multiplicity of infection of these assays was approximately 0.01.

C. Plate Format

The format of the test plate was standardized as follows. Each plate contains cell control wells (cells only), virus control wells (cells plus virus), drug cytotoxicity wells (cells plus drug only), drug colorimetric control wells (drug only), as well as experimental wells (drug plus cells plus virus). The final volume in each well was 200 µl. Samples were evaluated with triplicate measurements using a checkerboard dilution scheme; each of 5 concentrations of drug A (AZT, 3TC, etc.) were evaluated in combination with 9 different concentrations of Compound A; antiviral efficacy and cellular cytotoxicity were monitored by MTS staining at the experimental endpoint.

2. MTS Staining for Cell Viability

At assay termination, the assay plates were stained with the soluble tetrazolium-based dye MTS (CellTiter96 Reagent, Promega) to determine cell viability and quantify compound toxicity. MTS is metabolized by the mitochondrial enzymes of metabolically active cells to yield a soluble formazan product, allowing the rapid quantitative analysis of cell viability and compound cytotoxicity. The MTS is a stable solution that does not require preparation before use. At termination of the assay, 20 µl of MTS reagent was added per well. The microtiter plates were then incubated 4-6 hrs at 37° C. for the HIV cytoprotection assay; the incubation intervals were chosen based on empirically determined times for optimal dye reduction. Adhesive plate sealers were used in place of the lids, the sealed plate was inverted several times to mix the soluble formazan product and the plate was read spectrophotometrically at 490/650 nm with a Molecular Devices Vmax plate reader.

Analysis and Discussion

Analysis of drug combination assays was performed utilizing the anti-HIV assay methodology described above with statistical evaluations performed according to the method of Prichard and Shipman (Antiviral Research 14:181-206 [1990]). Combination antiviral assays were performed with CEM-SS cells utilizing the HIV-1$_{IIIB}$ strain of virus as described above. Five concentrations of drug (AZT, 3TC, PMPA, Efavirenz, indinavir, nelfinavir, AZT/3TC, or PMPA/3TC) were tested in various combinations with nine concentrations of Compound A. Effects of the drug combinations were calculated based on the activity of each compound when tested alone.

The expected additive antiviral protection was subtracted from the experimentally determined antiviral activity at each combination concentration resulting in a positive value (synergy), a negative value (antagonism), or zero (additivity). The results of the combination assays are presented three dimensionally at each combination concentration, yielding a surface of activity extending above (synergy) or below (antagonism) the plane of additivity. The volume of the surface is calculated and expressed as a synergy volume (µM$^2$%) calculated at the 95% confidence interval.

For these studies, synergy is defined as drug combinations yielding synergy volumes greater than 50 µM$^2$%. Slightly synergistic activity and highly synergistic activity have been defined as yielding synergy volumes of 50-100 µM$^2$% and >100 µM$^2$%, respectively. Additive drug interactions have synergy volumes in the range of −50 µM$^2$% to 50 µM$^2$%, while synergy volumes less than −50 µM$^2$% are considered slightly antagonistic or antagonistic (<−100 µM$^2$%). Table I provides the results of this study.

TABLE 1

| Compound | Synergy/Antagonism Volume (µM$^2$ %) | | | Mean Synergy/Antagonism Volume (µM$^2$ %; n = 3) |
|---|---|---|---|---|
| | Result 1 | Result 2 | Result 3 | |
| AZT | 46/−21 | 19/−44 | 57/−23 | 40.7/−29.3 |
| 3TC | 57/−7 | 84/−23 | 62/−30 | 67.7/−20.0 |
| PMPA | 29/−23 | 43/−4 | 13/−60 | 28.3/−29.0 |
| EFV | 26/−9 | 54/0 | 26/−7 | 35.3/−5.3 |
| IDV | 57/−7 | 13/−23 | 10/−26 | 26.7/−18.7 |
| NFV | 44/−3 | 38/−3 | 20/−46 | 34./−17.3 |
| AZT/3TC | 152/−2 | 74/−28 | 109/−9 | 111.7/−13.0 |
| PMPA/3TC | 32/−23 | 19/−21 | 50/−29 | 33.7/−24.3 |

Figure 2:
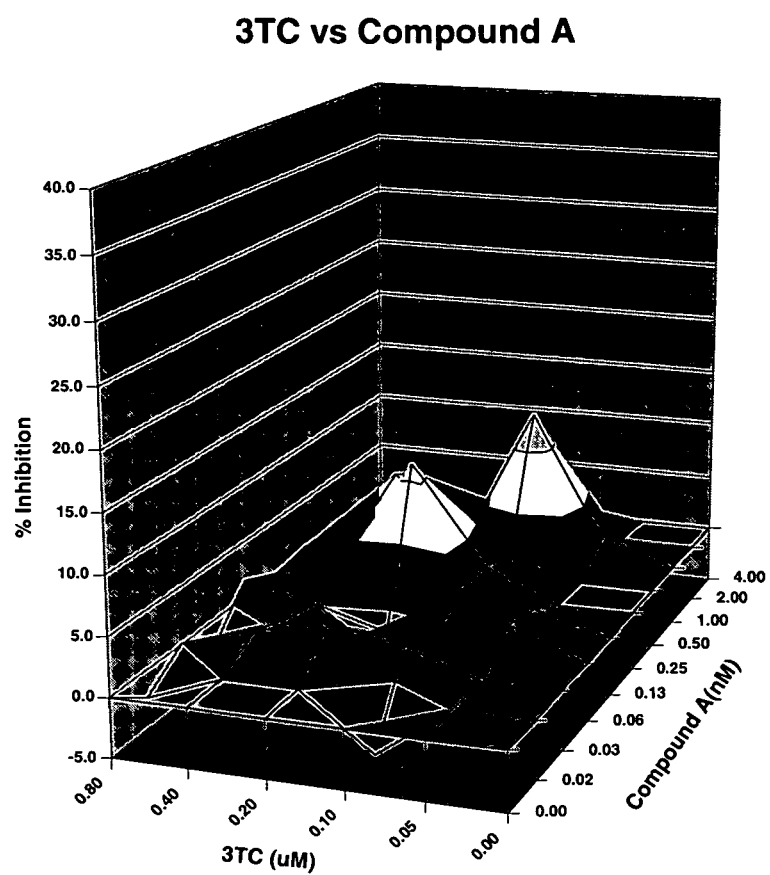
FIG. 2. Averaged 3-Dimensional Graph (n=3) for Drug Combination Assay of Compound A with 3TC. Percent inhibition of viral-induced cell death versus independent concentrations of Compound A and 3TC.
Figure 3:
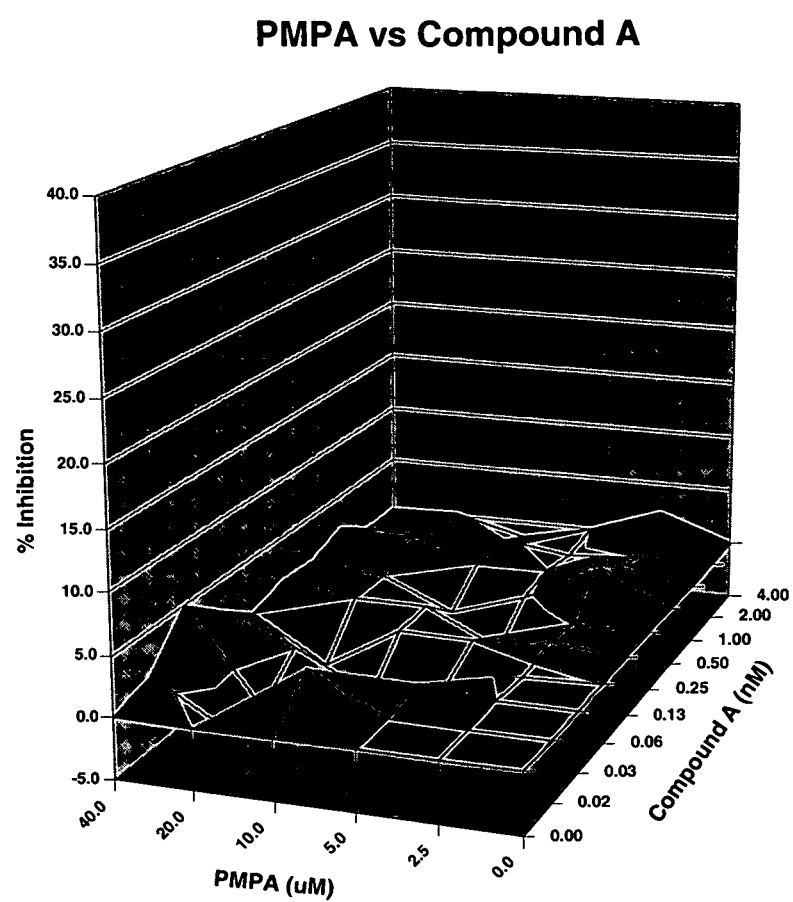
FIG. 3. Averaged 3-Dimensional Graph (n=3) for Drug Combination Assay of Compound A with PMPA. Percent inhibition of viral-induced cell death versus independent concentrations of Compound A and PMPA.
Figure 4:
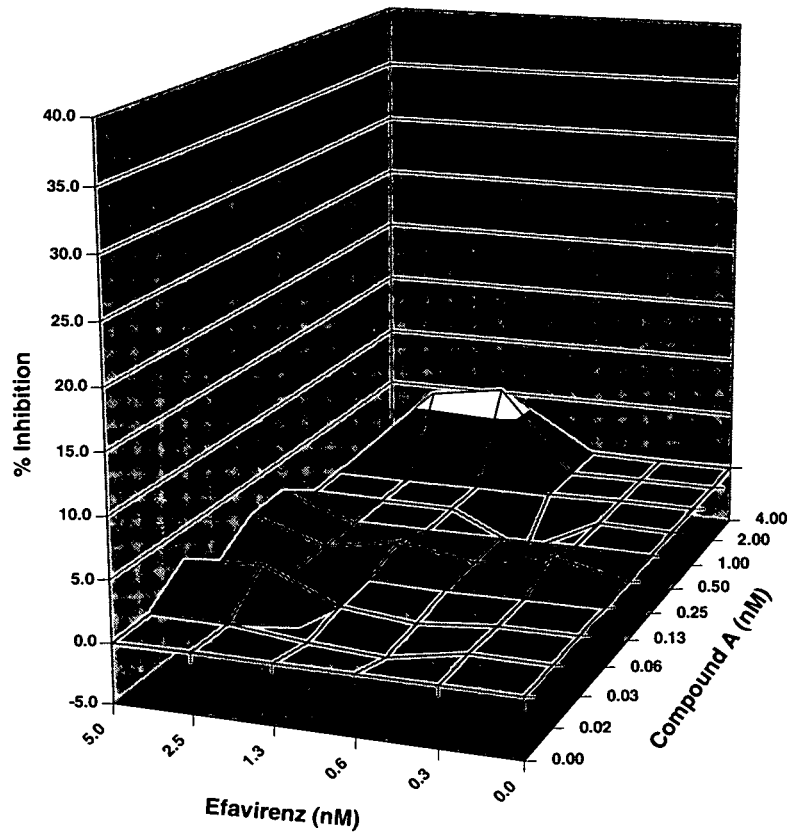
FIG. 4. Averaged 3-Dimensional Graph (n=3) for Drug Combination Assay of Compound A with efavirenz. Percent inhibition of viral-induced cell death versus independent concentrations of Compound A and efavirenz.
Figure 5:
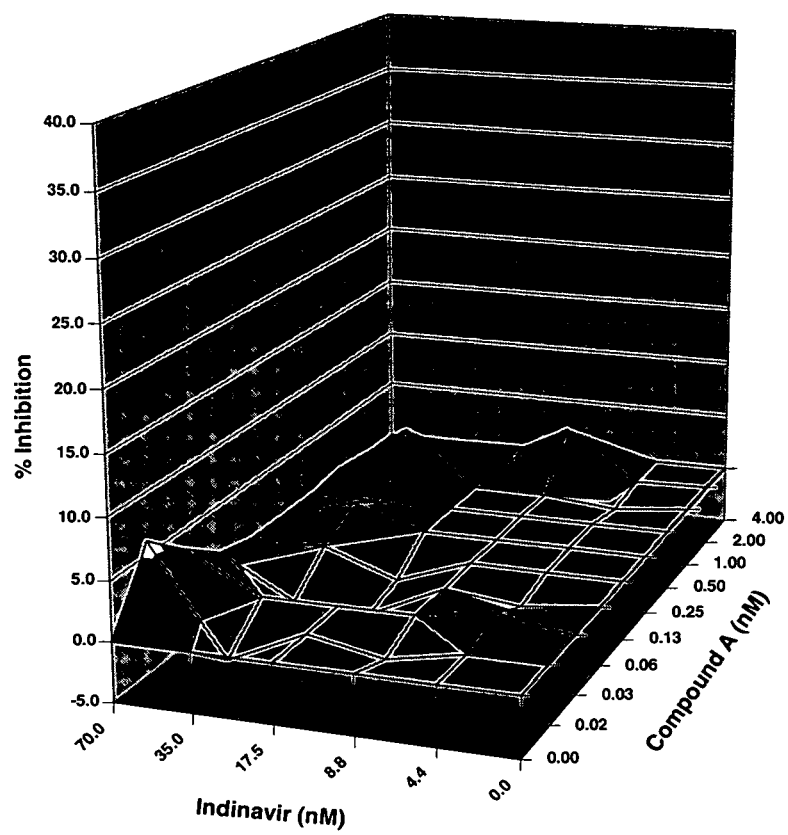
FIG. 5. Averaged 3-Dimensional Graph (n=3) for Drug Combination Assay of Compound A with indinavir. Percent inhibition of viral-induced cell death versus independent concentrations of Compound A and indinavir.
Figure 6:
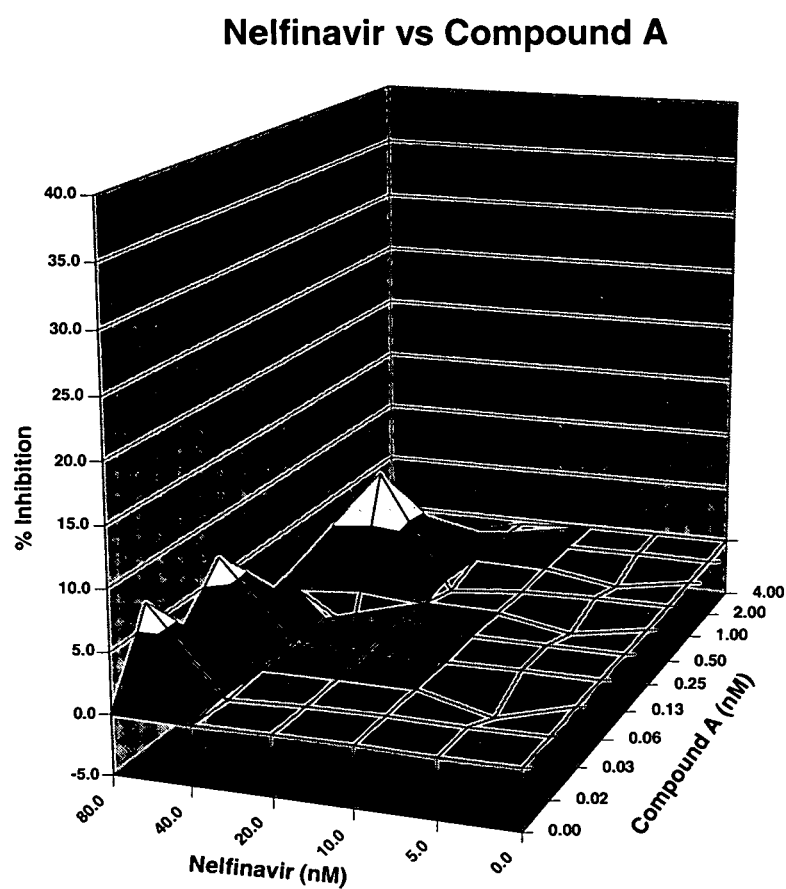
FIG. 6. Averaged 3-Dimensional Graph (n=3) for Drug Combination Assay of Compound A with nelfinavir. Percent inhibition of viral-induced cell death versus independent concentrations of Compound A and nelfinavir.
Figure 7:
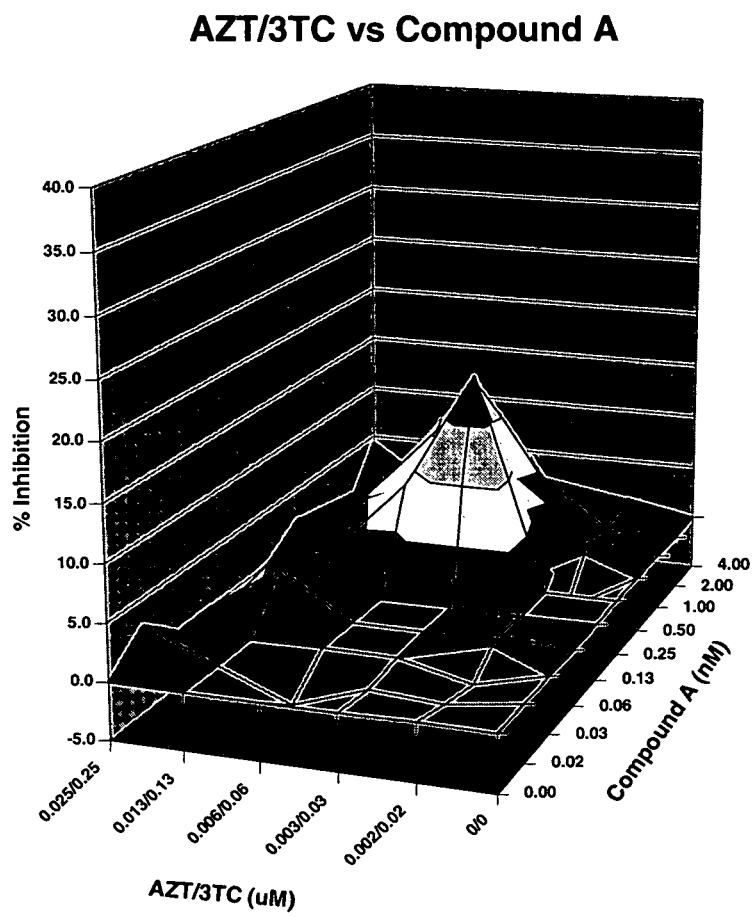
FIG. 7. Averaged 3-Dimensional Graph (n=3) for Drug Combination Assay of Compound A with AZT/3TC. Percent inhibition of viral-induced cell death versus independent concentrations of Compound A and AZT/3TC.
Figure 8:
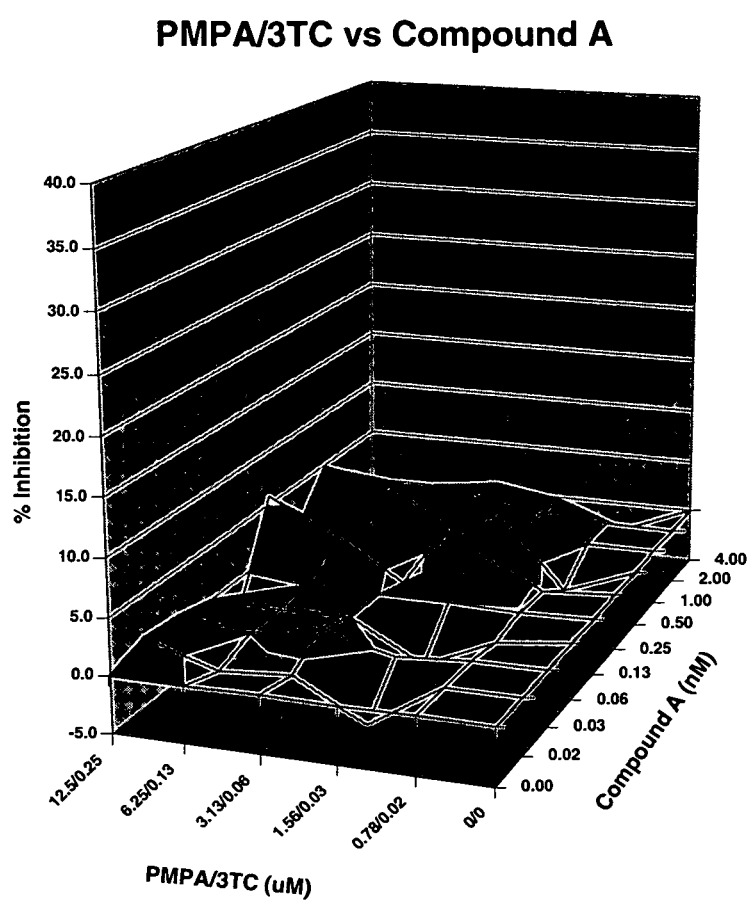
FIG. 8. Averaged 3-Dimensional Graph (n=3) for Drug Combination Assay of Compound A with PMPA/3TC. Percent inhibition of viral-induced cell death versus independent concentrations of Compound A and PMPA/3TC.

As summarized in Table 1 above, and based on the synergy criteria defined above, Compound A exhibits slightly synergistic interactions with 3TC (67.7 µM$^2$%) and Compound A also functions in a synergistic manner with AZT/3TC (111.7 µM$^2$%) in a triple-drug combination assay. Inspection of the averaged 3-dimensional surface plots (see FIGS. 1-8; derived from the average of 3 separate combination assays) reveals the observed synergy is focused around Compound A concentrations of 0.5-2.0 nM and 3TC concentrations of 0.1-0.2 µM or AZT/3TC concentrations in the range of 0.003/0.03-0.013/0.13 µM. Compound A appears to act in an additive manner with AZT, PMPA, efavirenz, indinaivr, nelfinavir, and PMPA/3TC. It should be noted that the MacSynergy software utilizes the individual triplicate data at 45 different drug-combinations to generate the 3-dimensional surface plots with their associated statistical 95% confidence intervals. As such, the observed synergy between Compound A and AZT/3TC predicted by the Prichard and Shipman MacSynergy model is significant. Analysis of this combination data by other analytical methods (e.g., Chou and Talalay, Adv. Enzyme Regul. 22:27-55, 1984) yield similar synergy observations, but the Median-Effect equation derived by Chou (Mol. Pharmacol. 10:235-247, 1974) lacks the statistical confidence intervals associated with the MacSynergy analysis.

There was no evidence of synergistic cytotoxicity within the drug concentrations examined for Compound A (4 nM high-test concentration). None of the drugs were cytotoxic within the concentration ranges evaluated. There are no notable synergistic cytotoxicities observed at concentrations where the drugs display potent antiviral properties.

The foregoing is merely illustrative of the invention and is not intended to limit the invention to the disclosed combinations or methods.

The instant application includes a Statement Accompanying Sequence Listing, and a Sequence Listing in both paper and computer-readable formats.

The invention claimed is:

1. A method for treating an HIV infectious disease in a human patient comprising administering to the patient a combination of:
   (a) an effective amount of (S)-6-(3-Chloro-2-fluorobenzyl)-1-(1-hydroxymethyl-2-methylpropyl)-7-methoxy-4-oxo-1,4-dihydroquinoline-3-carboxylic acid or a pharmaceutically acceptable solvate or salt thereof,
   (b) an effective amount of tenofovir disoproxil fumarate, and
   (c) an effective amount of emtricitabine.

2. The method of claim 1, wherein (a) and (b) and (c) are formulated together and administered as a single therapeutic composition.

3. A method for treating an HIV infectious disease in a human patient comprising administering to the patient a combination of:
   (a) an effective amount of (S)-6-(3-Chloro-2-fluorobenzyl)-1-(1-hydroxymethyl-2-methylpropyl)-7-methoxy-4-oxo-1,4-dihydroquinoline-3-carboxylic acid or a pharmaceutically acceptable solvate or salt thereof,
   (b) an effective amount of GS-7340, and
   (c) an effective amount of emtricitabine.

4. The method of claim 3, wherein (a) and (b) and (c) are formulated together and administered as a single therapeutic composition.

5. A composition for treating an HIV infectious disease in a human patient comprising:
   (a) an effective amount of (S)-6-(3-Chloro-2-fluorobenzyl)-1-(1-hydroxymethyl-2-methylpropyl)-7-methoxy-4-oxo-1,4-dihydroquinoline-3-carboxylic acid or a pharmaceutically acceptable solvate or salt thereof,
   (b) an effective amount of tenofovir disoproxil fumarate, and
   (c) an effective amount of emtricitabine.

6. A composition for treating an HIV infectious disease in a human patient comprising:

(a) an effective amount of (S)-6-(3-Chloro-2-fluorobenzyl)-1-(1-hydroxymethyl-2-methylpropyl)-7-methoxy-4-oxo-1,4-dihydroquinoline-3-carboxylic acid or a pharmaceutically acceptable solvate or salt thereof,
(b) an effective amount of GS-7340, and
(c) an effective amount of emtricitabine.

* * * * *

UNITED STATES PATENT AND TRADEMARK OFFICE
CERTIFICATE OF CORRECTION

| | | |
|---|---|---|
| PATENT NO. | : 8,633,219 B2 | Page 1 of 1 |
| APPLICATION NO. | : 11/133463 | |
| DATED | : January 21, 2014 | |
| INVENTOR(S) | : Matsuzaki et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1800 days.

Signed and Sealed this
Twenty-ninth Day of September, 2015

Michelle K. Lee
*Director of the United States Patent and Trademark Office*

SEQUENCE LISTING

```
<160> NUMBER OF SEQ ID NOS: 4

<210> SEQ ID NO 1
<211> LENGTH: 32
<212> TYPE: DNA
<213> ORGANISM: Artificial Sequence
<220> FEATURE:
<223> OTHER INFORMATION: Donor plus strand for activity determination
      of HIV integrase.

<400> SEQUENCE: 1
acccttttag tcagtgtgga aaatctctag ca                                     32

<210> SEQ ID NO 2
<211> LENGTH: 31
<212> TYPE: DNA
<213> ORGANISM: Artificial Sequence
<220> FEATURE:
<223> OTHER INFORMATION: Donor minus strand for activity determination
      of HIV integrase.

<400> SEQUENCE: 2
actgctagag attttccaca ctgactaaaa g                                      31

<210> SEQ ID NO 3
<211> LENGTH: 20
<212> TYPE: DNA
<213> ORGANISM: Artificial Sequence
<220> FEATURE:
<223> OTHER INFORMATION: Target plus strand for activity determination
      of HIV integrase.

<400> SEQUENCE: 3
tgaccaaggg ctaattcact                                                   20

<210> SEQ ID NO 4
<211> LENGTH: 20
<212> TYPE: DNA
<213> ORGANISM: Artificial Sequence
<220> FEATURE:
<223> OTHER INFORMATION: Target minus strand for activity determination
      of HIV integrase.

<400> SEQUENCE: 4
agtgaattag cccttggtca                                                   20
```